United States Patent
Ge et al.

(10) Patent No.: US 10,501,562 B2
(45) Date of Patent: Dec. 10, 2019

(54) CO-INITIATOR AND CO-MONOMER FOR USE IN PREPARING POLYMER RELATED COMPOSITIONS, METHODS OF MANUFACTURE, AND METHODS OF USE

(71) Applicant: University of Kansas, Lawrence, KS (US)

(72) Inventors: Xueping Ge, Lawrence, KS (US); Qiang Ye, Lawrence, KS (US); Paulette Spencer, Parkville, MO (US); Jennifer Ann Chadwick, Boston, MA (US); Linyong Song, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 93 days.

(21) Appl. No.: 15/548,053

(22) PCT Filed: Mar. 17, 2016

(86) PCT No.: PCT/US2016/022860
§ 371 (c)(1),
(2) Date: Aug. 1, 2017

(87) PCT Pub. No.: WO2016/149488
PCT Pub. Date: Sep. 22, 2016

(65) Prior Publication Data
US 2018/0016365 A1    Jan. 18, 2018

Related U.S. Application Data

(60) Provisional application No. 62/134,961, filed on Mar. 18, 2015.

(51) Int. Cl.
| | | |
|---|---|---|
| C08F 2/50 | (2006.01) | |
| C08F 4/00 | (2006.01) | |
| C08F 220/18 | (2006.01) | |
| C07C 271/20 | (2006.01) | |
| A61K 6/00 | (2006.01) | |
| A61K 6/083 | (2006.01) | |
| C07C 271/16 | (2006.01) | |
| C08F 222/22 | (2006.01) | |

(52) U.S. Cl.
CPC .............. *C08F 2/50* (2013.01); *A61K 6/0052* (2013.01); *A61K 6/083* (2013.01); *C07C 271/16* (2013.01); *C07C 271/20* (2013.01); *C08F 4/00* (2013.01); *C08F 220/18* (2013.01); *C08F 2222/225* (2013.01)

(58) Field of Classification Search
CPC .......... C08F 2/50; C08F 4/00; C08F 2220/18; C08F 2222/225; C08F 2222/1858; C08F 2222/1013; C08F 2222/1093; C07C 271/20; C07C 271/16; A61K 6/0023; A61K 6/083; A61K 6/0052; C08L 33/10
See application file for complete search history.

(56) References Cited

U.S. PATENT DOCUMENTS

| | | |
|---|---|---|
| 8,338,499 B2 | 12/2012 | Loccufier et al. |
| 2009/0170015 A1 | 7/2009 | Murakami et al. |
| 2014/0377717 A1 | 12/2014 | Wang et al. |

FOREIGN PATENT DOCUMENTS

EP    1616897    3/2010

OTHER PUBLICATIONS

Ge, X, et al., "Synthesis and evaluation of a novel co-initiator for dentin adhesives: Polymerization kinetics and leachables study", Journal of the Minerals, Metals, and Materials Society, E-Pub., Feb. 27, 2015; vol. 767, No. 4, pp. 796-803.
International Search Report and Written Opinion of PCT/US2016/022860, dated Jul. 25, 2016.

*Primary Examiner* — Sanza L. McClendon
(74) *Attorney, Agent, or Firm* — Ray Quinney & Nebeker, P.C.; Paul N. Taylor

(57) ABSTRACT

The present disclosure relates to tertiary amine co-initiators that demonstrate reduced leaching and which may be utilized in dental restoration and other biomedical applications. Embodiments of the present disclosure provide compounds and compositions for use in preparing polymers and light curable dental resin composites, as well as methods for preparing photocurable polymer-based dental restorative materials. In one or more disclosed embodiments, a co-initiator for use in preparing a polymer comprises a tertiary amine core and two or more pendant, terminal methacrylate groups. In some embodiments, the co-initiator may also act as a co-monomer in a co-polymerization reaction.

20 Claims, 14 Drawing Sheets

FIG. 1A

| 3-Component Photoinitiator System (Photosensitizer / Amine Co-Initiator / Iodonium Salt) | | |
|---|---|---|
| Photosensitizer | Camphorquinone (CQ) | |
| Iodonium Salt | Diphenyliodonium Hexafluorophosphate (DPIHP) | |
| Co-Initiator (Electron Donor) | Ethy-4-(Dimethylamino) Benzoate (EDMAB); 2-(Dimethylamino) Ethyl Methacrylate (DMAEMA); TUMA | |

| Monomer System | | |
|---|---|---|
| 2-Hydroxyethylmethacrylate (HEMA) | Bisphenol A glycerolate Dimethacrylate (BisGMA) | |

FIG. 5

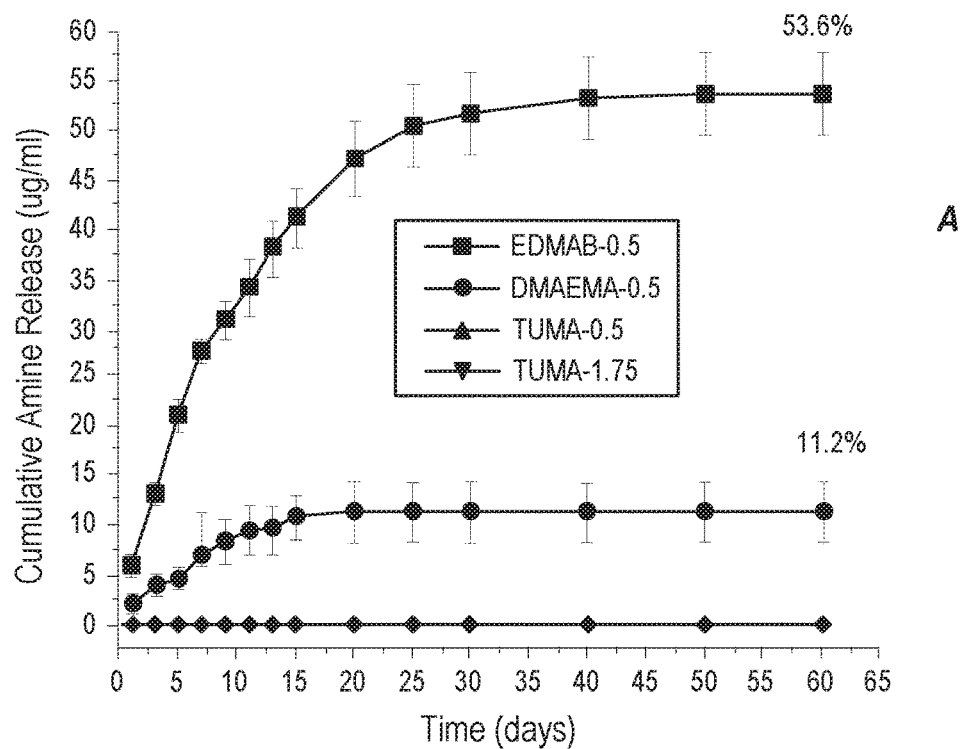
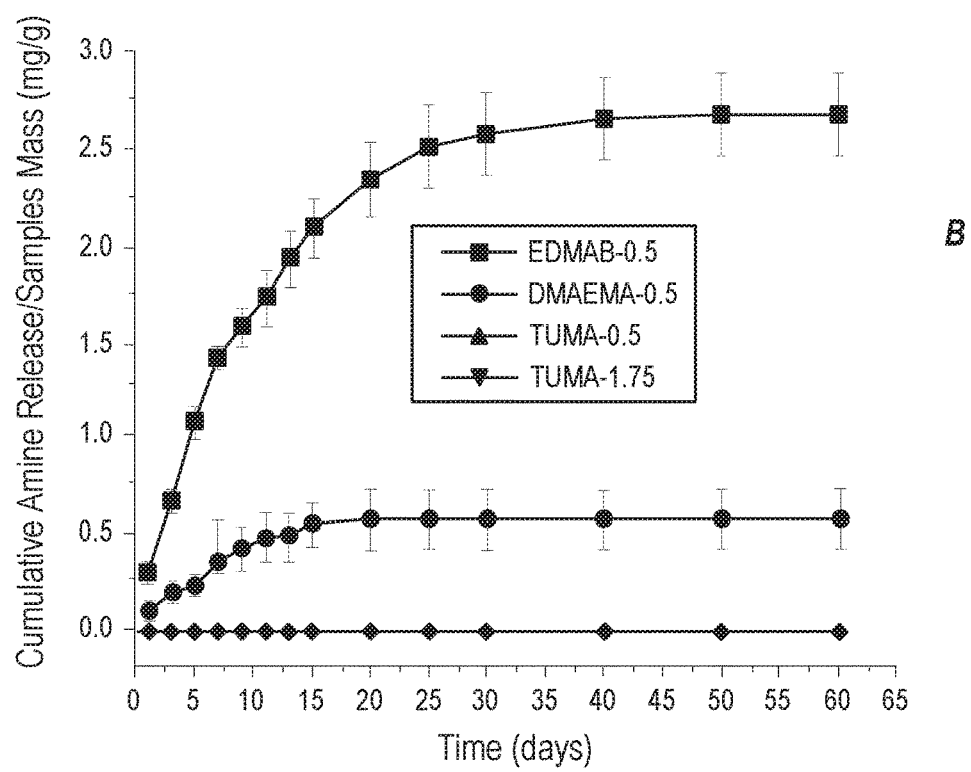
FIG. 7

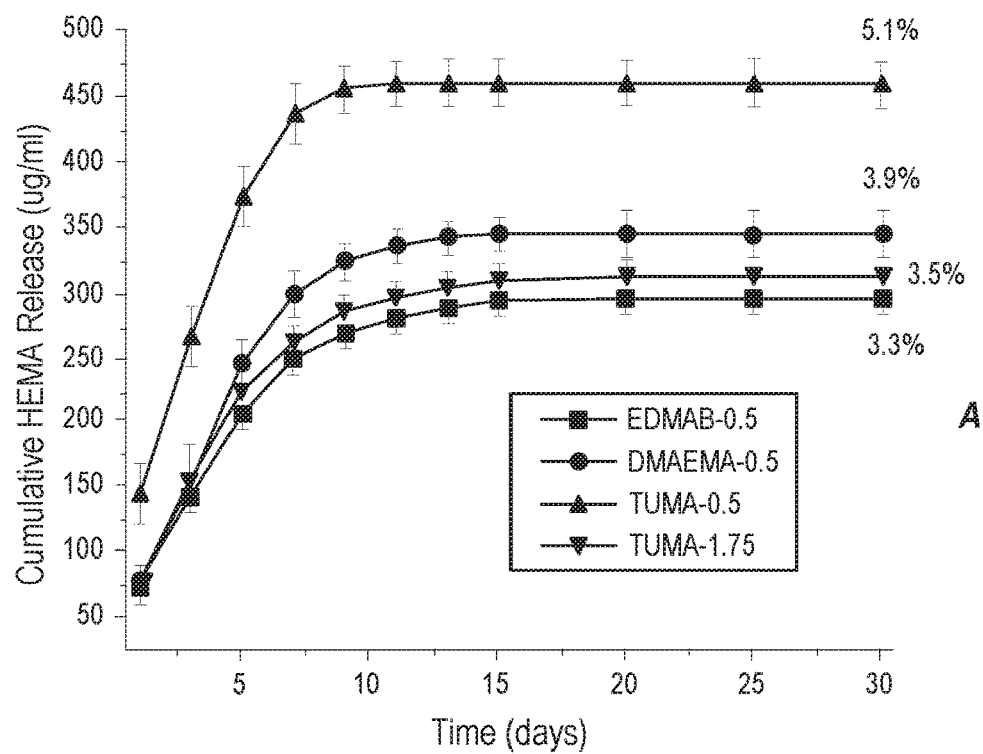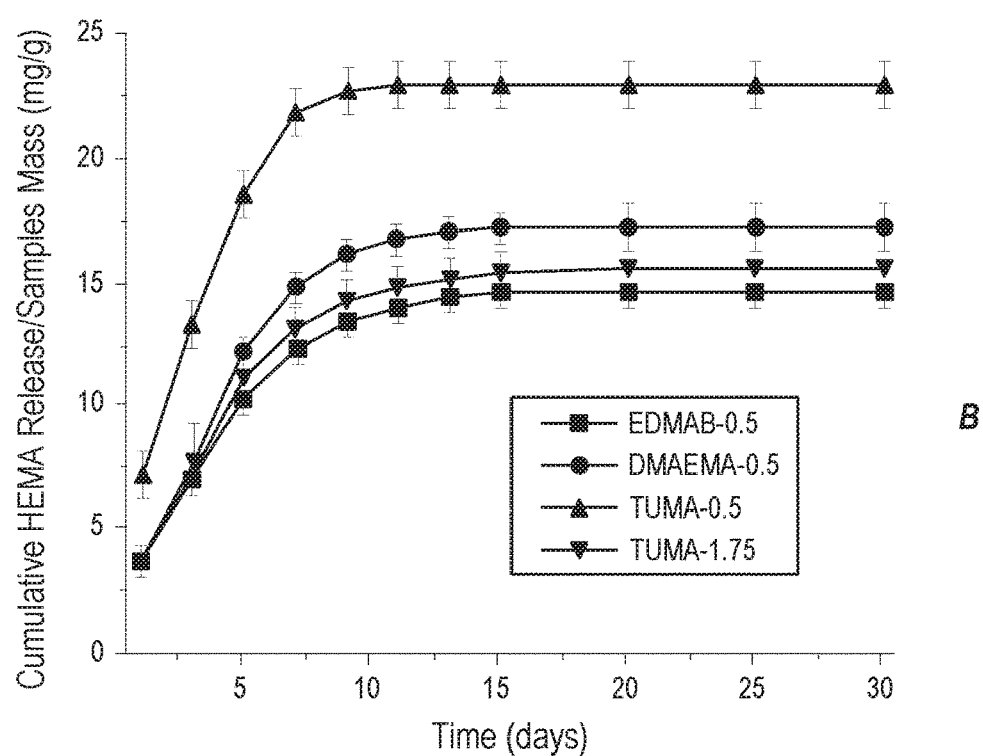
FIG. 8

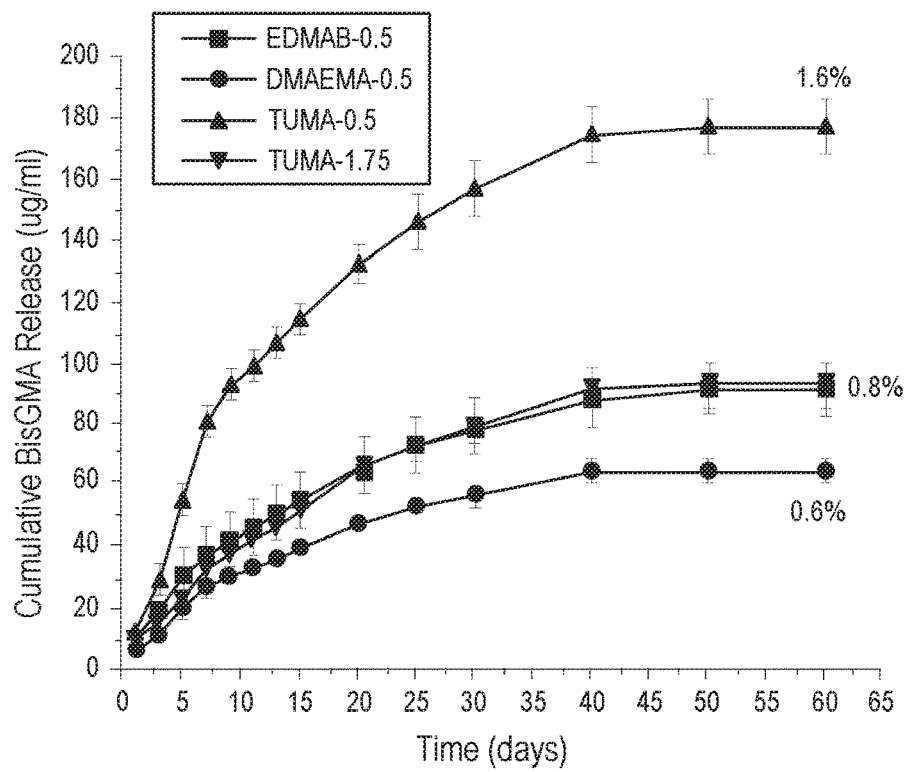
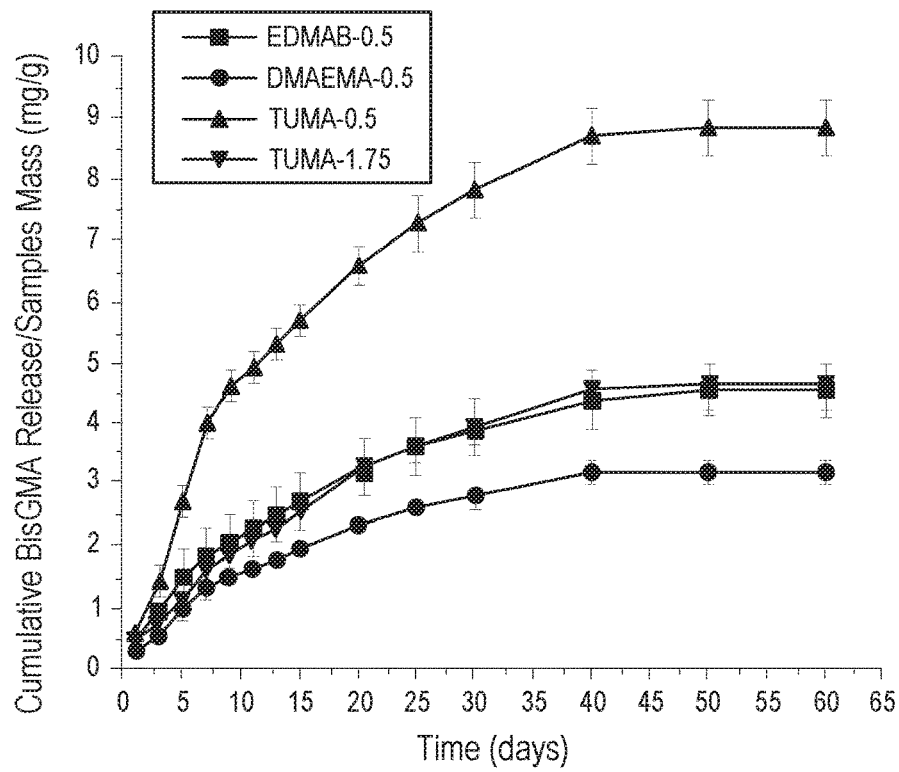
FIG. 9

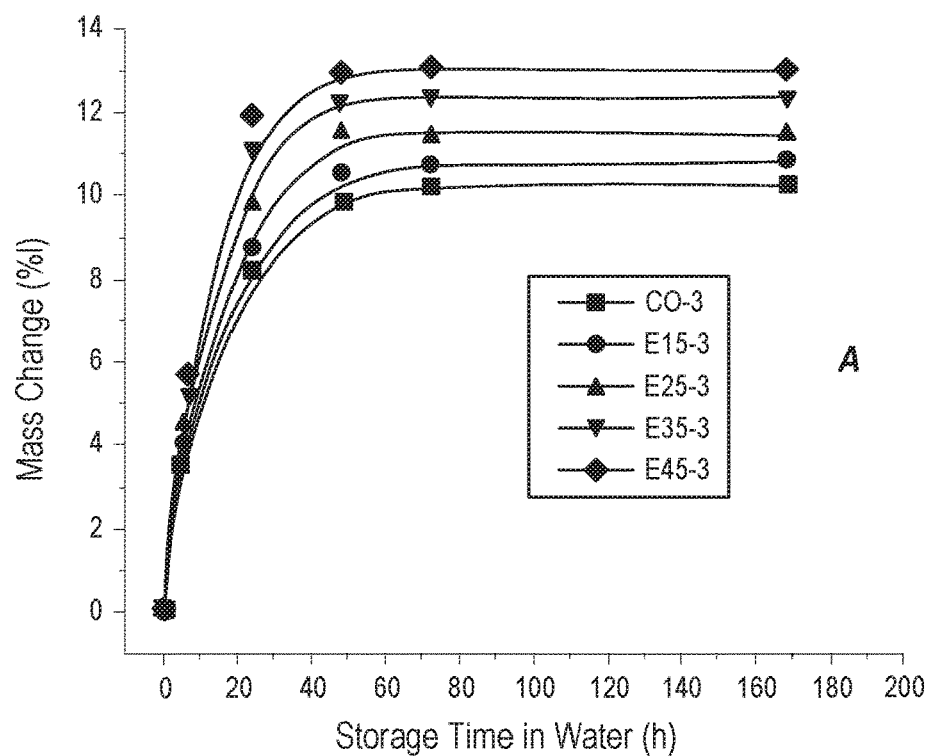
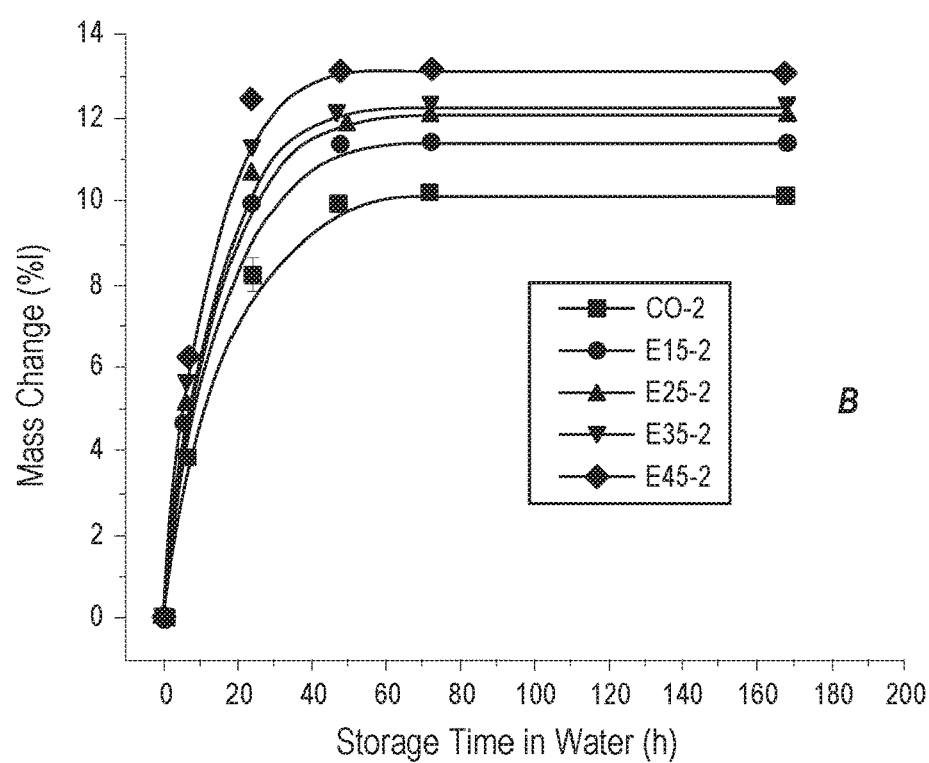
FIG. 14

CO-INITIATOR AND CO-MONOMER FOR USE IN PREPARING POLYMER RELATED COMPOSITIONS, METHODS OF MANUFACTURE, AND METHODS OF USE

CROSS REFERENCE TO RELATED APPLICATIONS

This application is a U.S. Nationalization of PCT Application Number PCT/US2016/022860, filed on Mar. 17, 2016, which claims the benefit of U.S. Provisional Patent Application Ser. No. 62/134,961 filed on Mar. 18, 2015, entitled "NOVEL TERTIARY AMINE CO-INITIATOR FOR DENTAL COMPOSITIONS AND OTHER BIO-MEDICAL APPLICATIONS WITH REDUCED LEACHING", which are herein incorporated by reference in their entireties.

STATEMENT OF GOVERNMENT INTEREST

This invention was made with government support under R01_DE014392, and R01_DE022054, awarded by the National Institutes of Health. The U.S. government has certain rights in the invention.

BACKGROUND

1. Field of Disclosure

The present invention relates generally to the preparation of dental restorative compounds, compositions, composites, and adhesives that contain amine-based co-initiators and/or co-monomers, as well as materials for other applications where reduced leaching is desired and/or the use of UV light irradiation is unfavorable.

2. Related Technology

Various compounds, compositions, composites, and adhesives are made of or contain polymers and undergo phase changes as a result of a polymerization reaction or otherwise undergo chemical curing of the compounds, compositions, composites, or adhesives. This can be advantageous for repairing or binding materials and has applications in the automotive and construction industries, among others. The same or similar technology is used in dental procedures, including dental restorative procedures. Within the dental industry, there exist some compounds, compositions, composites, and adhesives that are provided in multi-part systems that rely on visible light for polymerization initiation. These systems commonly include, among other things, an amine-based co-initiator to be used as an electron donor.

BRIEF SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Embodiments of the present disclosure provide compounds and compositions for use in preparing polymers and light curable dental resin composites, as well as methods for preparing photocurable polymer-based dental restorative materials. In one or more embodiments, a co-initiator for use in preparing a polymer comprises a tertiary amine core and two or more pendant, terminal methacrylate groups. In some embodiments, the foregoing co-initiator may also act as a co-monomer in a co-polymerization reaction.

In one or more additional or alternative embodiments, compositions are provided for use in preparing a light curable dental resin composite and may include a co-initiator that comprises a tertiary amine core and two or more pendant, terminal methacrylate groups, and in some embodiments, compositions may further include a photosensitizer and/or a diaryliodonium and/or a sulfonium salt.

Compositions provided in one or more embodiments may additionally or alternatively include monomers or oligomers selected from monomers or oligomers having one or more ethylenically unsaturated groups, di-acrylates and methacrylates, tri-acrylates and methacrylates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("BisGMA"), triethylene glycol dimethacrylate (TEGDMA), 1,6-bis-[2-methacryloyloxyethoxy-carbonylamino]-2,4,4-trimethylhexane (UDMA), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof. In some embodiments, the monomers or oligomers included in compositions for use in preparing a light curable dental resin composite may comprise at least one of 2-hydroxyethyl methacrylate (HEMA) and diglycidyl methacrylate of bisphenol (BisGMA), monomers or oligomers of the co-initiator, itself, or combinations thereof.

Implementations of the present disclosure further provide methods for preparing a photocurable polymer-based dental restorative material. In one or more embodiments, the method may include the step of combining a set of one or more monomers or oligomers with a photoinitiator system. The method may also include the step of exposing the combined set of one or more monomers or oligomers and photoinitiator system to light. The method may also include the step of polymerizing the set of one or more monomers or oligomers to yield a polymer.

In one or more embodiments of the foregoing methods, the set of one or more monomers or oligomers may be selected from monomers or oligomers having one or more ethylenically unsaturated groups, di-acrylates and methacrylates, tri-acrylates and methacrylates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("BisGMA"), triethylene glycol dimethacrylate (TEGDMA), 1,6-bis-[2-methacryloyloxyethoxycarbonylamino]-2,4,4-trimethylhexane (UDMA), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof. In one or more additional or alternative embodiments, the one or more monomers or oligomers may comprise 2-hydroxyethyl methacrylate (HEMA), diglycidyl methacrylate of bis-phenol (BisGMA), a co-initiator comprising a tertiary amine core and two or more pendant, terminal methacrylate groups, or combinations thereof.

In one or more embodiments of the foregoing methods, the photoinitiator system may comprise a co-initiator that comprises a tertiary amine core and two or more pendant, terminal methacrylate groups. In one or more additional or alternative embodiments, the photoinitiator system may comprise a photosensitizer and/or a diaryliodonium or a sulfonium salt.

In one or more embodiments, the methods for preparing a photocurable polymer-based dental restorative material yield a polymer. The polymer yielded as a result of one or more of the disclosed methods may be prepared in the mouth of a subject (e.g., in-situ, chair-side) and may additionally or alternatively leach substantially no co-initiator following polymerization.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 5 is a chart detailing the name and associated chemical formulas for camphorquinone (CQ), diphenyliodonium hexafluorophosphate (DPIHP), 2-hydroxyethylmethacrylate (HEMA), ethyl-4-(dimethylamino) benzoate (EDMAB), 2-(dimethylamino) ethyl methacrylate (DMAEMA), TUMA, and 2,2-Bis[4-(2-hydroxy-3-methacryloxypropoxy) phenyl]-propane (bisphenol A glycerolate dimethacrylate or BisGMA).

FIG. 7A is a graph illustrating cumulative amino co-initiator release from dentin adhesives as a function of incubation time in ethanol in accordance with one or more examples disclosed herein.

FIG. 7B is a graph illustrating the data from FIG. 7A transformed by a calculation that divided the mass value of released compounds by the mass values of polymer samples in accordance with one or more examples disclosed herein.

FIG. 8A is a graph illustrating cumulative HEMA release from dentin adhesives with different co-initiators as a function of incubation time in ethanol in accordance with one or more examples disclosed herein.

FIG. 8B is a graph illustrating the data from FIG. 8A transformed by a calculation that divided the mass value of released compounds by the mass values of polymer samples in accordance with one or more examples disclosed herein.

FIG. 9A is a graph illustrating cumulative BisGMA release from dentin adhesives with different co-initiators as a function of incubation time in ethanol in accordance with one or more examples disclosed herein.

FIG. 9B is a graph illustrating the data from FIG. 9A transformed by a calculation that divided the mass value of released compounds by the mass values of polymer samples in accordance with one or more examples disclosed herein.

FIGS. 14A-14B are graphs that illustrate water sorption of resin polymers cured with different weight contents of TUMA; symbols E15, E25, E35, and E45 represent 15, 25, 35, and 45 wt. % of TUMA, respectively; formulations depicted in FIG. 14A had a three-component (CQ, DPIHP, and EDMAB) initiator system and formulations depicted in FIG. 14B had a two-component (CQ and DPIHP) initiator system all in accordance with one or more examples disclosed herein.

DETAILED DESCRIPTION

Figure 1A:
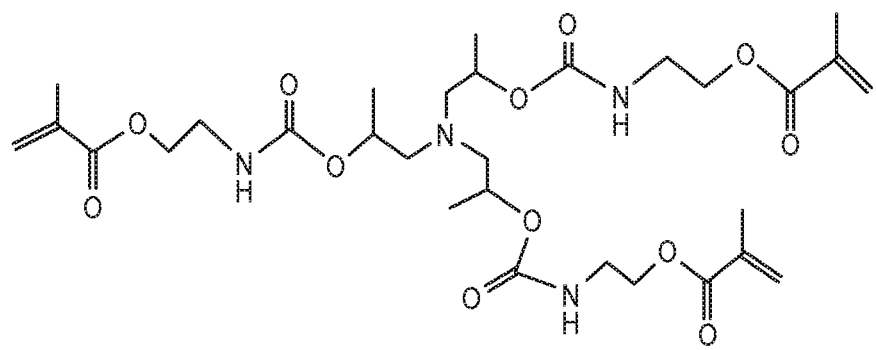
FIGS. 1A-1C illustrate exemplary co-initiators, and each illustrated co-initiator comprises a tertiary amine core and two or more pendant, terminal methacrylate groups according to implementations of the present disclosure.

1. Overview of Amine-Based Co-Initiators in the Dental Industry

Polymer-based composites have become the most common dental restorative material and are used more than twice as often as amalgam filling materials. These resin composites fulfill many of the requirements for clinical restorative applications, including excellent aesthetics and high mechanical properties. Despite the importance of these materials, the polymer resins of these systems have remained largely unchanged since its introduction several decades ago. Dimethacrylate-based resins have been commonly used for dental restorative materials but are plagued by a critical problem: there is often not complete conversion of the methacrylates, leaving unreacted material that can be extracted into the oral environment. The release of unreacted methacrylic monomers, together with compounds of the polymerization initiator system from dental materials, has been considered as a source of a wide variety of adverse biological reactions, including local and systemic toxicity, pulp reactions, allergic and estrogenic effects.

The initiator system exerts considerable influence on the degree of conversion of the monomers and on the behavior of dental materials in the wet, oral environment. A three-component system for visible light initiation has been widely used in dental restoratives; the initiator system generally contains a light absorbing photosensitizer (predominantly camphorquinone, hereinafter CQ), an electron donor serving as a co-initiator (which may be an amine compound), and a third component has recently been added that improves the visible light induced photopolymerization (often a diaryliodonium or sulfonium salt). The electron donating co-initiator can play a critical role in the photoinitiation process, and the type of co-initiator as well as its ratio to the photosensitizer used in the initiator system influences the resulting polymerization quality. However, there are some biocompatibility concerns when using many amine co-initiators, which limits their suitability for use as co-initiators in dental restorative materials. For example, it has been demonstrated that unreacted co-initiators used in dental restorative materials may elute from the cured polymers, and if the co-initiator is amine-based, it may cause cytotoxicity, pulpal irritation, allergic, and/or estrogenic effects.

Ethyl-4-(dimethylamino) benzoate (EDMAB), which is a very effective hydrogen donor, has been widely used as a co-initiator in combination with CQ in dental resins formulations. However, as with many amine-based co-initiators, EDMAB poses serious biocompatibility issues. EDMAB is an aromatic amine, and it cannot be co-polymerized into the polymer network leaving it largely or entirely unreacted with the polymer and free to cause its potential cytotoxic effects. Another co-initiator, 2-(dimethylamino) ethyl methacrylate (DMAEMA), carries a methacrylate group and has improved biocompatibility when compared with EDMAB, likely as a result of its ability to co-polymerize with methacrylate-monomers. A CQ/DMAEMA photoinitiator system is a common system used in photoactivated dental materials. However, the stability of DMAEMA is problematic. DMAEMA has been reported to degrade up to 82% during 24 hours in the presence of water, and the degradation products contain organic amine compounds, which may cause biocompatibility issues similar to or the same as those described above for most amine-based co-initiators.

Current dental composite systems also face problems with longevity. The average clinical lifetime of posterior composite resin restorations is roughly 5.7 years and is mostly due to secondary decay or fracture. A dominant reason for failure of composite restorations is secondary decay, and clinically, the failure occurs most often at the composite/tooth interface.

Generally, the dental composite is too viscous to bond directly to the tooth, and thus, a low viscosity adhesive may be used to form a bond between the tooth and the composite. The integrity of the adhesive and the adhesive/tooth bond can be important for the durability of resin-based dental restorations, and the lack of durable and effective dentin adhesives compounds the problems facing the use of composites in restorative dentistry.

Polymerizable monomers or oligomers are often added to the photoinitiation systems to form dentin adhesives. The monomers used in dentin adhesives can be critical and monomer selection exerts considerable influence on the properties, durability, and behavior of dentin adhesives in the wet, oral environment. Much attention and effort has been devoted to the development of new monomers in the quest to develop dentin adhesives that provide durable bonding at the composite/tooth interface.

Clearly, the stability and biocompatibility issues of current amine-based co-initiators and the need for dentin adhesives that provide durable bonding at the composite/tooth interface allow for advantages to be realized in the field of dental restorative compounds, composites, and adhesives, among other fields. The present disclosure provides a tertiary amine co-initiator, which may additionally or alternatively act as a co-monomer, for use in a plethora of materials, including dental adhesives, resins, compositions, composites, and/or cements. In some embodiments, for example, the tertiary amine co-initiator of the present disclosure leaches substantially no co-initiator following polymerization, making it excellent for biocompatibility. One or more of the disclosed tertiary amine co-initiators and/or co-monomers may, in some embodiments, be used within similar or different materials in other fields or industries, including, for example, within tissue engineering or within other biomedical applications.

2. A Tertiary Amine as a Co-Initiator

In one or more embodiments of the present disclosure, a co-initiator is provided for use in preparing a polymer, wherein the co-initiator comprises a tertiary amine core and two or more pendant, terminal methacrylate groups. At least three such chemical structures are detailed in FIGS. 1A, 1B, and 1C. Referring now to FIG. 1C, depicted is a compound having a tertiary amine core and three side groups. The tertiary amine core, as depicted, comprises three separate side groups, each having a terminal methacrylate group. In one embodiment, the tertiary amine core may have a single side group having a terminal methacrylate core, and in another embodiment, the tertiary amine core may comprise at least two side groups, wherein each of the at least two side groups may have a pendant, terminal methacrylate group.

With continued reference to FIG. 1C, each depicted side group may be characterized as a methacrylate-R2-R1-alkyl side group attached to a tertiary amide backbone. In one or more embodiments of the present disclosure, at least one of the foregoing side groups may have R groups, R1 and R2, where R1 is selected from the group consisting of hydrogen, an alkyl, a hydroxyl, and an amino, and R2 is selected from the group consisting of an ether, an amido, an amino, an alkyl-ether, an alkyl-amido, an alkyl-amino, an ether-alkyl, an amido-alkyl, an amino-alkyl, an alkyl-ether-alkyl, an alkyl-amido-alkyl, and an alkyl-amino-alkyl. Any R groups described herein, unless specified otherwise, may be substituted or unsubstituted.

A number of exemplary side groups are available based on the foregoing and may include, but are not limited to: methacrylate-ether-alkyl, methacrylate-ether-hydroxyl-alkyl, methacrylate-ether-amino-alkyl, methacrylate-amido-alkyl, methacrylate-amido-hydroxyl-alkyl, methacrylate-amido-amino-alkyl, methacrylate-amino-alkyl, methacrylate-amino-hydroxyl-alkyl, methacrylate-amino-alkyl, methacrylate-alkyl-ether-alkyl, methacrylate-alkyl-ether-hydroxyl-alkyl, methacrylate-alkyl-ether-amino-alkyl, methacrylate-alkyl-amido-alkyl, methacrylate-alkyl-amido-hydroxyl-alkyl, methacrylate-alkyl-amido-amino-alkyl, methacrylate-alkyl-amino-alkyl, methacrylate-alkyl-amino-hydroxyl-alkyl, methacrylate-alkyl-amino-alkyl, methacrylate-ether-alkyl, methacrylate-ether-alkyl-hydroxyl-alkyl, methacrylate-ether-alkyl-amino-alkyl, methacrylate-amido-alkyl, methacrylate-amido-alkyl-hydroxyl-alkyl, methacrylate-amido-alkyl-amino-alkyl, methacrylate-amino-alkyl, methacrylate-amino-alkyl-hydroxyl-alkyl, methacrylate-amino-alkyl-amino-alkyl, methacrylate-alkyl-ether-alkyl, methacrylate-alkyl-ether-alkyl-hydroxyl-alkyl, methacrylate-alkyl-ether-alkyl-amino-alkyl, methacrylate-alkyl-amido-alkyl, methacrylate-alkyl-amido-alkyl-hydroxyl-alkyl, methacrylate-alkyl-amido-alkyl-amino-alkyl, methacrylate-alkyl-amino-alkyl, methacrylate-alkyl-amino-alkyl-hydroxyl-alkyl, methacrylate-alkyl-amino-alkyl-amino-alkyl, or combinations thereof.

Any of the foregoing alkyl groups and any of the forthcoming alkyl groups disclosed herein may preferably comprise an alkyl having a carbon chain length of $(C_1-C_{22})$, $(C_1-C_{16})$, $(C_1-C_{12})$, more preferably a carbon chain length of $(C_1-C_8)$, $(C_1-C_6)$, $(C_1-C_4)$, and most preferably a carbon chain length of $(C_1-C_3)$.

In one or more embodiments, the tertiary amide backbone of FIG. 1C may be connected to two or more side groups, wherein each and/or all of the side groups may comprise any of the foregoing exemplary side groups in any combination. In one embodiment, each of two or more side groups attached to the tertiary amide backbone is the same. In one embodiment, each of the two or more side groups attached to the tertiary amide backbone is different.

Figure 1B:
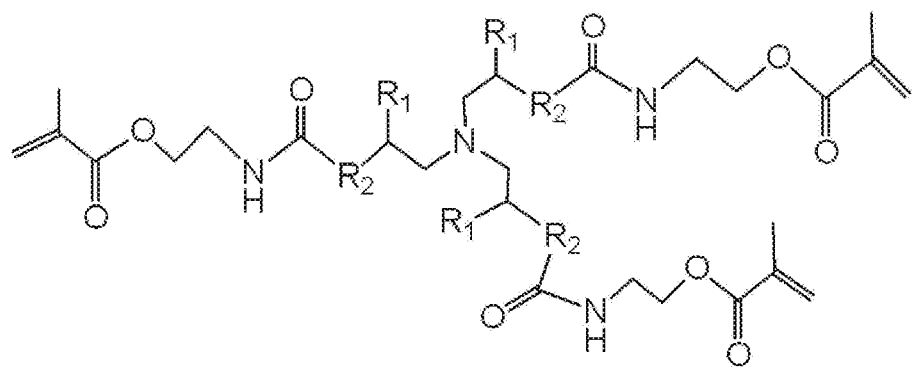
Figure 1C:
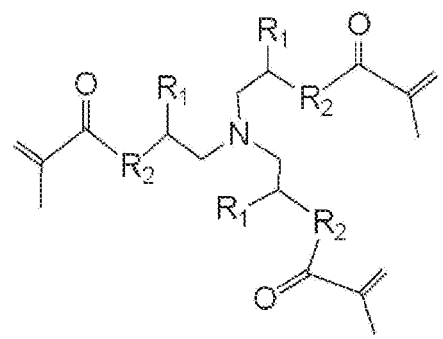

Referring now to FIG. 1B, depicted is a compound having a tertiary amine core and three side groups. The tertiary amine core, as depicted, comprises three separate side groups, each side group having a terminal methacrylate group. In one embodiment, the tertiary amine core may comprise a single side group having a terminal methacrylate core, and in another embodiment, the tertiary amine core may comprise at least two side groups, wherein each of the at least two side groups may include a pendant, terminal methacrylate group.

With continued reference to FIG. 1B, each depicted side group may be characterized as a methacrylate-alkyl-amido-R2-R1-alkyl side group attached to a tertiary amide backbone. In one or more embodiments of the present disclosure, at least one of the foregoing side groups may have R groups, R1 and R2, where R1 is selected from the group consisting of hydrogen, an alkyl, a hydroxyl, and an amino and R2 is selected from the group consisting of an ether and an amino.

A number of exemplary side groups are available based on the foregoing and may include, but are not limited to: methacrylate-alkyl-amido-ether-alkyl, methacrylate-alkyl-amido-ether-hydroxyl-alkyl, methacrylate-alkyl-amido-ether-amino-alkyl, methacrylate-alkyl-amido-amino-alkyl, methacrylate-alkyl-amido-amino-hydroxyl-alkyl, methacrylate-alkyl- or combinations thereof.

In one or more embodiment, the tertiary amide backbone of FIG. 1B may be connected to two or more side groups, wherein each and/or all of the side groups may comprise any of the foregoing exemplary side groups in any combination. In one embodiment, each of two or more side groups attached to the tertiary amide backbone is the same. In one embodiment, each of the two or more side groups attached to the tertiary amide backbone is different.

Referring now to FIG. 1A, depicted is a compound having a tertiary amine core and three side groups. The tertiary amine core, as depicted, comprises three separate side groups, each having a terminal methacrylate group. In one embodiment, the tertiary amine core may have a single side group having a terminal methacrylate core, and in another embodiment, the tertiary amine core may comprise at least two side groups, wherein each of the at least two side groups may have a pendant, terminal methacrylate group. Each depicted side group may be characterized as a methacrylate-alkyl-amido-ether-alkyl side group attached to a tertiary amide backbone.

In some embodiments, the compound depicted in FIG. 1A may be denoted (8-(2-(((2-(methacryloyloxy)ethyl)carbamoyl)oxy)propyl)-6,10-dimethyl-4,12-dioxo-5,11-dioxa-3,8,13-triazapentadecane-1,15-diyl bis(2-methylacrylate)) and may otherwise be referred to herein as TUMA. In one or more embodiments, TUMA may act as a co-initiator for use in preparing a polymer. Additionally or alternatively, any of the compounds illustrated in FIGS. 1A, 1B, 1C, derivatives thereof, and other co-initiators having a tertiary amine core and two or more pendant, terminal methacrylate groups may act as co-initiators for use in preparing a polymer.

In some embodiments, the co-initiator may be used to prepare a polymer to be part of a compound, composite, and/or adhesive. For example, a co-initiator having a tertiary amine core and two or more pendant, terminal methacrylate groups may be a co-initiator used to prepare a polymer to be used in a dental restorative material. Additionally or alternatively, a co-initiator having a tertiary amine core and two or more pendant, terminal methacrylate groups may be a co-initiator used to prepare a light curable dental resin composite. For example, the co-initiator may be part of a system for visible and/or UV light initiation in dental resin composites, and the system may include a light absorbing photosensitizer (e.g., CQ or an equivalent photosensitizer) and may also include a diaryliodonium or sulfonium salt (e.g., DPIHP or an equivalent diaryliodonium or sulfonium salt).

In one embodiment, the above system for visible light initiation in dental resin composites may further include monomers or oligomers selected from monomers or oligomers having one or more ethylenically unsaturated groups, di-acrylates and methacrylates, tri-acrylates and methacrylates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("BisGMA"), triethylene glycol dimethacrylate (TEGDMA), 1,6-bis-[2-methacryloyloxyethoxycarbonylamino]-2,4,4-trimethylhexane (UDMA), bis[1-(2-acryloxyl]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof. In one or more embodiments, the monomers or oligomers comprise at least one of HEMA and BisGMA.

Accordingly, in some embodiments, the system for visible light initiation in dental resin composites may include one or more of (and in some embodiments all of): a co-initiator having a tertiary amine core and two or more terminal methacrylate groups, a photosensitizer, a diaryliodonium or sulfonium salt, and one or more monomers or oligomers. In one embodiment, photoactivating the system initiates polymerization of the monomers to form a polymer. In one embodiment, the polymer may be a dental resin composite and/or a dental adhesive and/or a dental cement. In some embodiments, the same or similar system may provide a polymer for tissue engineering or another biomedical application.

In one or more embodiments, a similar or different method than the foregoing is provided to prepare a photocurable polymer-based dental restorative material. The method may comprise the step of combining a set of one or more monomers or oligomers with a photoinitiator system, wherein the photoinitiator system comprises a co-initiator comprising a tertiary amine core and two or more pendant, terminal methacrylate groups. The method may further comprise the step of exposing the combined set of one or more monomers or oligomers and photoinitiator system to light. The method may further comprise the step of polymerizing the set of one or more monomers or oligomers to yield a polymer.

In one or more embodiments, the one or more monomers or oligomers are selected from the same group of monomers and oligomers as described above for the system for visible light initiation in dental resin composites, which includes, for example, the monomers or oligomers being HEMA and BisGMA. In one or more embodiment, the method of preparing a photocurable polymer-based dental restorative material may further comprise a photoinitiator system that includes a photosensitizer and/or a diaryliodonium or a sulfonium salt.

In one embodiment, any method of preparing a photocurable polymer-based dental restorative material within the scope of this disclosure may be practiced with patients, and the polymer may be prepared in a mouth of a subject and/or patient.

3. A Tertiary Amine as a Co-Monomer

In the one or more embodiments described above and other embodiments, a co-initiator having a tertiary amine core and two or more pendant, terminal methacrylate groups may also act as a co-monomer in a co-polymerization reaction or may be the sole monomer or oligomer within the composition and/or set of one or more monomers or oligomers. Said another way, in one or more embodiments, the monomer or oligomers of the above compositions and/or the set of one or more monomers may individually comprise the co-initiator as the monomer or oligomer within the composition and/or set of one or more monomers or oligomers, or the monomers and oligomers of the above compositions and/or the set of one or more monomers may comprise only one of the monomers or oligomers. For example, the monomers and oligomers may comprise the co-initiator and at least one of HEMA and BisGMA.

In some embodiments, the two or more pendant, terminal methacrylate groups of the co-initiator/monomer may participate as reactants and/or substrates in the polymerization process. Accordingly, one or more resulting polymers utilizing a co-initiator having a tertiary amine core and two or more pendant, terminal methacrylate groups as monomers (which in some embodiments may be within a photocurable polymer-based restorative material, a light curable dental resin composite, or similar) may leach substantially no co-initiator following polymerization as the co-initiator may double as the polymerizing monomer. The co-initiator may thus become incorporated into the cured polymer.

Light curable compositions according to the present invention may thus include a co-initiator (e.g., TUMA) as described herein. One or more additional polymerizable components (e.g., monomers and/or oligomers) may be further included, such as HEMA, BisGMA, or other polymerizable components including one or more ethylenically unsaturated groups. The composition may further include a photoinitiator system, such as any of those described herein, or any other that will be apparent to one of skill in the art. For example, CQ, DPIHP, and/or EDMAB may be included to aid in initiating photopolymerization. Amine activators other than the tertiary amine (e.g., TUMA) as described herein may not be needed, although they may be included, if desired. Examples of such activators include benzoyl peroxide. Other amine activators will be apparent to those of skill in the art. Advantageously, use of the tertiary amine co-initiator as described herein allows the TUMA or other tertiary amine to be incorporated into the polymerized product, so that the tertiary amine is a co-monomer in the polymerization reaction, making any leaching that might otherwise occur much less likely.

By way of example, the tertiary amine co-initiator (e.g., TUMA, or any of the compounds described in conjunction with FIGS. 1A-1C) may be included in any suitable range of the composition. By way of example, such tertiary amine co-initiator including two or more terminal methacrylate groups may be included in an amount of at least 0.5%, at least 1%, at least 3%, at least 5%, from 5% to 80%, from 5% to 70%, from 5% to 60%, from 5% to 50%, from 10% to 50%, or from 15% to 45% by weight of the composition.

Other polymerizable components may be included within the composition, as described herein. Such other polymerizable components may be included from greater than 0%, greater than 1%, greater than 3%, up to 80%, up to 70%, up to 60%, up to 50%, from 5% to 50%, from 10% to 40%, from or from 10% to 35% by weight.

Of course, camphorquinone, or another photoinitiator may be included, e.g., typically at a value of less than 3%, or less than 1% by weight. Amine activators other than the methacrylate terminated tertiary amine may be included, if desired, e.g., in amounts of less than 3%, or less than 1% by weight.

Where a diaryliodonium or a sulfonium salt are included, such may be present in an amount of up to 5%, up to 3%, or up to 1%, by weight, as desired.

Various other components, such as fillers (e.g., an inorganic filler) may be included within the light curable composition, if desired, as will be appreciated by those of skill in the art. The amount of such an included filler may vary widely, e.g., from 0% up to 90%, up to 80%, up to 70%, up to 60%, up to 50%, from 5% to 50%, or from 10% to 40%. Such a filler may increase strength of the resulting polymerized composite.

The ranges disclosed herein may refer to weight fractions of the various components of the mixed composition (e.g., the two-part composition) as a whole. They may also refer to the weight fractions relative to the part of the composition in which they are initially provided, before mixing. The two parts may typically be mixed at a 1:1 ratio. Additionally or alternatively, the two parts (HEMA/BisGMA) may typically be mixed at a ratio from 1:2 to 2:1).

4. Examples

The following examples are illustrative and should not be interpreted as limitations to the invention. With respect to chemicals used in any of Examples 1-12, 2,2-Bis[4-(2-hydroxy-3-methacryloxypropoxy) phenyl]-propane (bisphenol A glycerolate dimethacrylate or BisGMA; obtained from Polysciences, Warrington, Pa.) and 2-hydroxyethylmethacrylate (HEMA; obtained from Acros Organics, NJ) were used as received without further purification, as monomers; camphorquinone (CQ), Ethyl-4-(dimethylamino) benzoate (EDMAB), diphenyliodonium hexafluorophosphate (DPIHP), and 2-(dimethylamino) ethyl methacrylate (DMAEMA) were obtained from Aldrich (Milwaukee, Wis.) and used without further purification; all other chemicals were obtained from Sigma-Aldrich at reagent grade and used without further purification. Some of the aforementioned chemical structures are provided in FIG. 5.

With respect to resin formulations disclosed within Examples 5-8, the resin portion of the formulations may include or consist of HEMA and BisGMA with a mass ratio of 45/55, which is similar to widely used commercial dentin adhesives. CQ (0.5 wt. %), amine co-initiator (0.5 wt. % or 1.75 wt. %), and DPIHP (1.0 wt. %), with respect to the total amount of monomers, are used as a three-component photoinitiator system. Three different amine co-initiators are used: EDMAB (0.5 wt. %), DMAEMA (0.5 wt. %), and TUMA (0.5 wt. % and 1.75 wt. %). It should be noted that the mole concentration is the same for the co-initiator with EDMAB at 0.5 wt. % and TUMA at 1.75 wt. %. The resin mixtures were prepared in brown glass vials and stirred for 48 h on an orbital shaker to form a homogeneous solution.

With respect to resin formulations disclosed within Examples 8-12, the monomer system contains BisGMA, HEMA, and TUMA at the mass ratio of 45/55-x/x. Two photoinitiator (PI) systems are compared. One initiator system contains three components: CQ, DPIHP, and EDMAB, and the second initiator system contains CQ and DPIHP. The control adhesive formulations are: CO-3: HEMA/BisGMA 45/55 w/w with a 3-component PI and CO-2: HEMA/BisGMA 45/55 w/w with a 2-component PI. These controls are used as a comparison to the experimental adhesive resins (Ex-3 or Ex-2), in which x represents the weight percentage of synthesized co-monomer (TUMA) to replace part of BisGMA. CQ, EDMAB, and DPIHP are used as a three-component-photoinitiator system (CO-3 and Ex-3 groups) at concentrations of 0.5, 0.5 and 1.0 wt % with relation to the total amount of monomers, respectively. The two-component-photoinitiator system contains only CQ (0.5 wt %) and DPIHP (1.0 wt %) (CO-2 and Ex-2 groups). The resin mixtures were prepared in brown glass vials and stirred for 48 h on an orbital shaker to form a homogeneous solution.

Example 1

Figure 2:
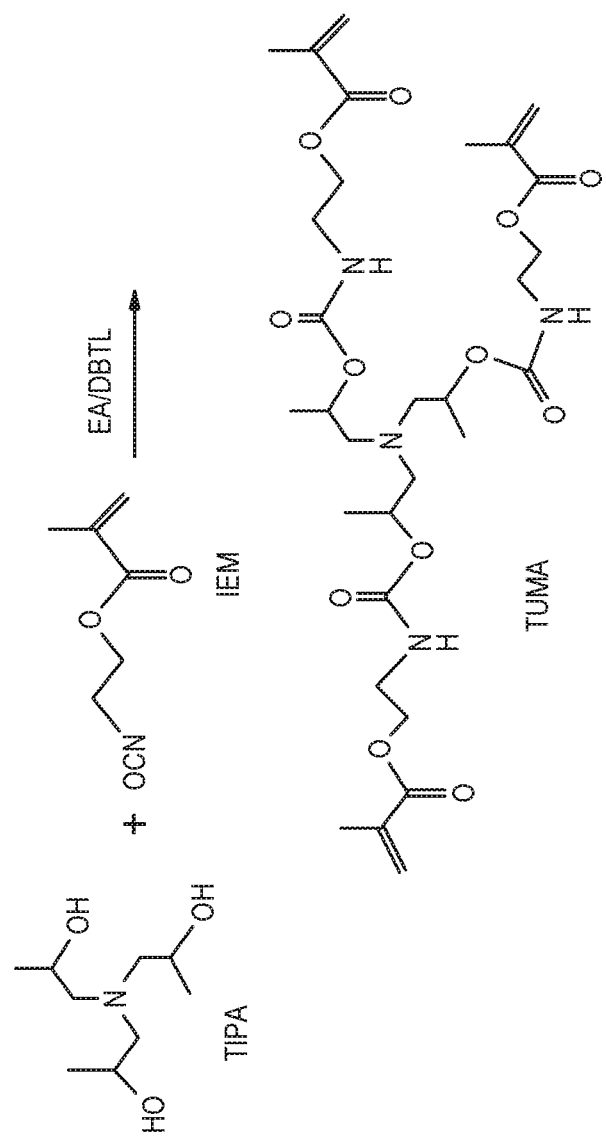
FIG. 2 illustrates a synthesis reaction of (8-(2-(((2-(methacryloyloxy)ethyl)carbamoyl)oxy)propyl)-6,10-dimethyl-4,12-dioxo-5,11-dioxa-3,8,13-triazapentadecane-1,15-diyl bis (2-methylacrylate)) (TUMA), a tertiary amine co-initiator having three pendant, terminal methacrylate groups in accordance with one or more examples disclosed herein.

The scheme for the chemical synthesis of TUMA is shown in FIG. 2. TUMA was synthesized in the following manner: 2-isocyantoethyl methacrylate (IEM, 25.6 g, 0.165 mol) with 30 mL dry ethyl acetate (EA) was added dropwise to a three-neck flask containing triisopropanolamine (TIPA, 10 g, 0.052 mol), dibutyltin dilaurate (DBTL, 0.03 g), and EA (50 mL). The solution was stirred continuously at 25° C. throughout the process. Following complete addition of IEM, the reaction was allowed to continue at room temperature for another 24 h. The reaction was monitored by thin-layer chromatography (mobile phase: dichloromethane). After reaction completion, the product-containing solution was purified by washing with distilled water and ethyl acetate until the solution was clear. The solution was dried over anhydrous $MgSO_4$ and the solvent was removed with a rotary evaporator at 35-40° C. The yield of this synthesis of TUMA, in its colorless, viscous state, was 95%. The chemical structure for TUMA is included in FIG. 1A, FIG. 2, and FIG. 5.

Example 2

Figure 3:
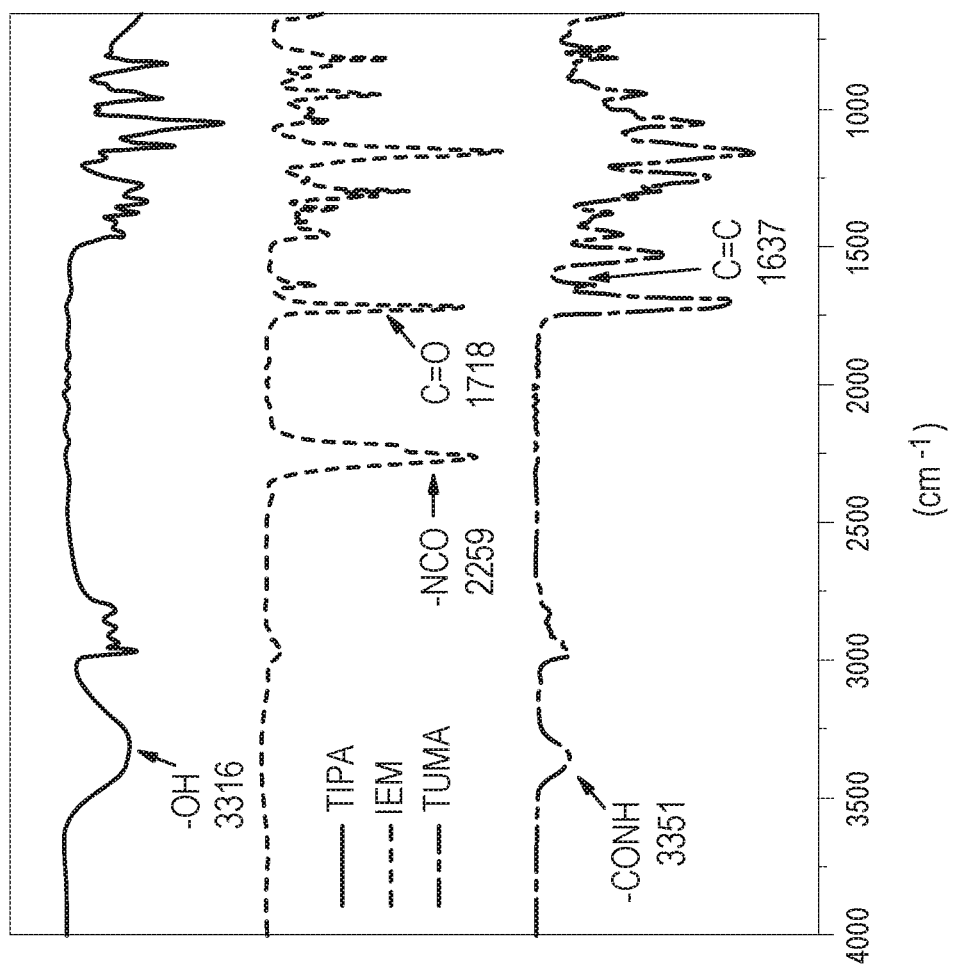
FIG. 3 illustrates a Fourier transform infrared spectra of triisopropanolamine (TIPA), 2-isocyantoethyl methacrylate (IEM), and TUMA in accordance with one or more examples disclosed herein.

The structure of newly synthesized amine co-initiator TUMA was identified using Fourier transform infrared (FTIR). The resultant FTIR spectra of TIPA, IEM, and TUMA are illustrated in FIG. 3. The characteristic FTIR peaks for TUMA are 3351 $cm^{-1}$ (NH stretching on —CONH) and 1637 $cm^{-1}$ (C=C bending on methacrylate groups). The disappearance of the —NCO of IEM stretching band at 2259 $cm^{-1}$ confirmed the formation of the new co-initiator.

Example 3

Figure 4:
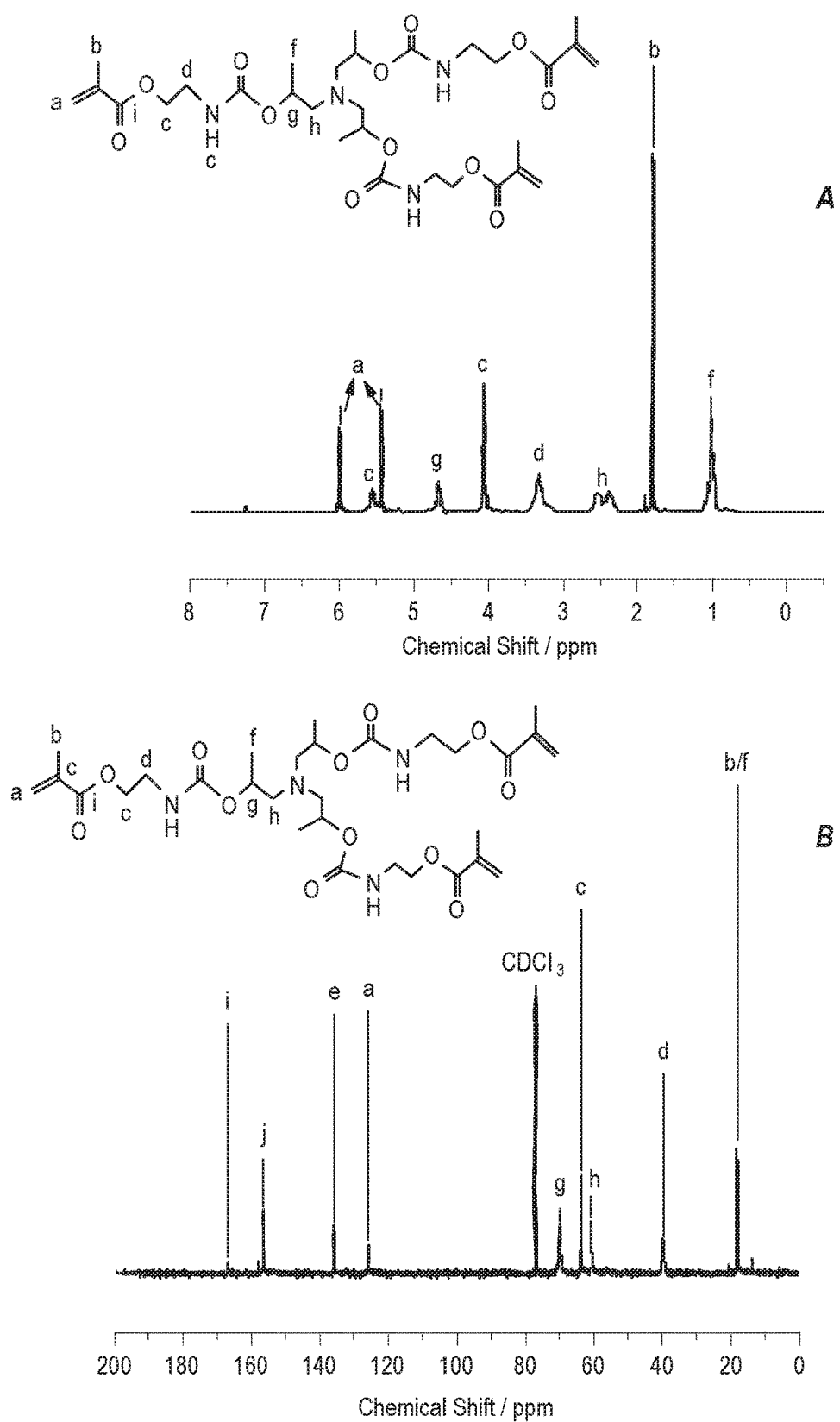
FIG. 4A illustrates a 1H nuclear magnetic resonance spectra of synthesized TUMA in accordance with one or more examples disclosed herein.
FIG. 4B illustrates a 13C nuclear magnetic resonance spectra of synthesized TUMA in accordance with one or more examples disclosed herein.

The purity of synthesized TUMA was characterized by analyzing its $^1H$ NMR and $^{13}C$ NMR spectra, which were obtained on a Bruker Advance DRX 500 spectrometer (Bruker AXS Inc., Madison, Wis.) equipped with a broadband probe. Deuterated chloroform ($CDCl_3$) was used as the solvent. FIG. 4A illustrates the $^1H$ nuclear magnetic resonance spectra of synthesized TUMA and FIG. 4B illustrates the $^{13}$C nuclear magnetic resonance spectra of synthesized TUMA.

The $^1$H NMR/$^{13}$C NMR spectra of TUMA show the chemical shifts, which confirm the desired structures. The methacrylate groups are supported by the presence of two singlets ($\delta$=6.15 ppm and 5.63 ppm) on the $^1$H NMR spectrum and by the peaks at 135.8 ppm and 125.8 ppm in the $^{13}$C NMR, assignable to the double bond of a methacrylate group.

Example 4

The chemical stability of three amine co-initiators (EDMAB, DMAEMA, and TUMA) was characterized by $^1$H NMR spectroscopy, which were obtained on a Bruker Advance DRX 500 spectrometer (Bruker AXS Inc., Madison, Wis.) equipped with a broadband probe. Deuterated dimethyl sulfoxide (DMSO-$d_6$)/deionized water (80/20 wt/wt) was used as the solvent. The NMR spectra of 0.04 M amine samples were monitored as a function of storage time at 25° C. The mixed (DMSO/water) solvent was used because of its ability to dissolve EDMAB and TUMA, which are hydrophobic compounds.

Figure 6:
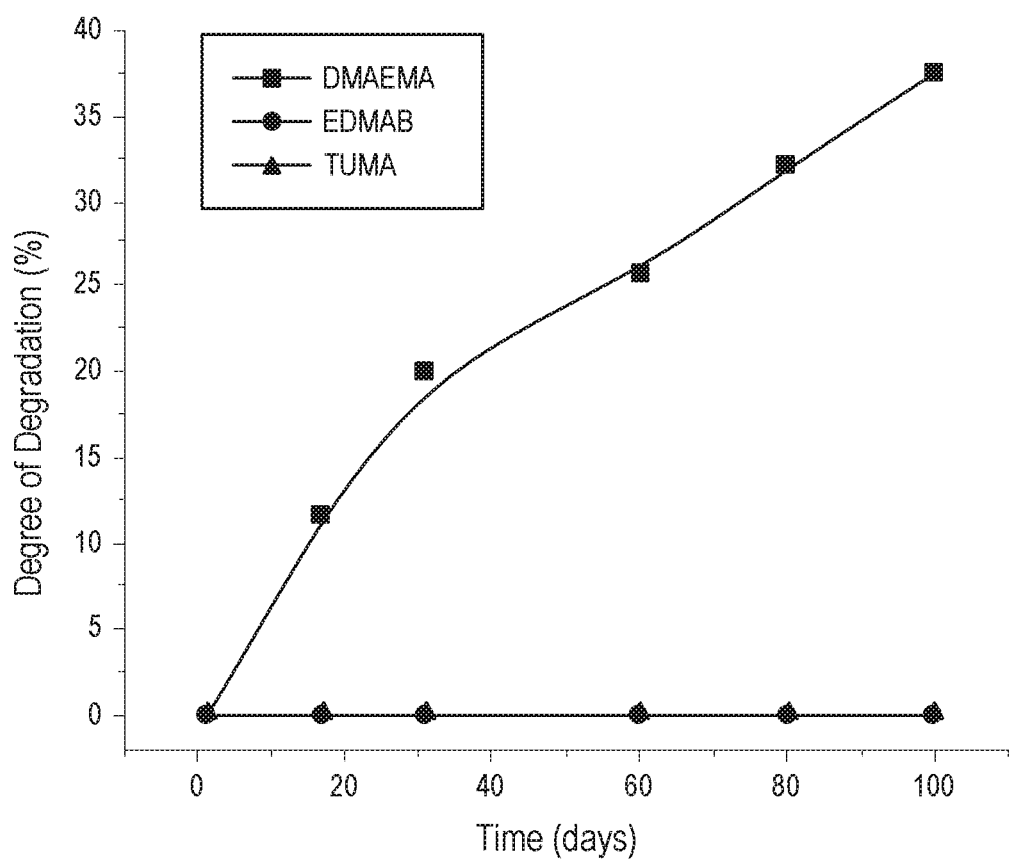
FIG. 6 is a graph illustrating the stability of three different amine co-initiators in DMSO-d6 with 20 wt. % H2O at a concentration of 0.04 M in accordance with one or more examples disclosed herein.

There is a rapid degradation rate for DMAEMA, with 37.6% degraded at 100 days. No degradation was detected for either EDMAB or TUMA after 100 days storage at 25° C. Thus, the chemical stability results indicate EDMAB and TUMA are more stable than DMAEMA, and the degree of conversion of the methacrylate monomers was comparable with EDMAB and DMAEMA when TUMA was used as the co-initiator at 1.75 wt. %. FIG. 6 illustrates a graph representing the foregoing stability results.

Example 5

FIG. 7A is a graph illustrating cumulative amino co-initiators release from dentin adhesives as a function of incubation time in ethanol, and FIG. 7B is a graph illustrating the data from FIG. 7A transformed by a calculation that divided the mass value of released compounds by the mass values of polymer samples. To determine the cumulative amine co-initiator release from dentin adhesives as a function of incubation time in ethanol, disk samples, which measured 4 mm diameter and 1 mm thick, were used. These samples were prepared by injecting the resin formulations into hermetic lids (T 120110; TA Instruments, New Castle, Del.) and covering with a glass coverslip (Prod No. 26023; Ted Pella, Inc., Redding, Calif.). Five specimens were prepared for each formulation. The samples were light polymerized with a 40 s exposure to a commercial light polymerization unit (Spectrum; Dentsply) at an intensity of 550 mW cm$^{-2}$. The polymerized samples were stored in the dark at room temperature for 48 h to provide adequate time for postcure polymerization. The samples were extracted and the mass was recorded. The samples were stored in 1 mL ethanol (200 proof) at 25° C. The solution was replaced with fresh ethanol and reserved for HPLC at fixed time intervals. The samples were centrifuged, and the supernatant was collected and analyzed by HPLC. Co-initiators and monomers released from the polymers were assayed by reverse phase HPLC (RPHPLC). This technique allows for the separation, identification, and quantification of individual molecules in complex mixtures.

A Shimadzu LC-HTC HPLC system (Shimadzu, Columbia, Md.) equipped with a SPD-M20A photodiode array detector, an autosampler with EZStart chromatography software as a controller and also for data processing, was used for this study. Separation was performed on a reversephase column A phenomenex Luna 5 lm C18 4.6 9 250 nm (Phenomenex, Torrance, Calif.) column and security guard cartridge were used to isolate the products. The mobile phase consisted of a mixture of a 10 mM potassium phosphate buffer and acetonitrile (CH$_3$CN). The pH of the buffer was adjusted to 7.0 with sodium hydroxide. The elution was started at a constant flow rate of 0.2 mL/min with CH$_3$CN: 10 mM potassium phosphate buffer (65:35, vol/vol) for 25 min and then ramped to 100% CH$_3$CN in 1 s and kept constant for 5 min. Twenty microliters of the supernatant were injected onto the HPLC column with a constant column temperature of 40° C. The ultraviolet spectrum at 208 nm wavelength was used to detect the leachables. Leached monomers and amine co-initiators were identified and quantified by comparison with reference compounds of known composition. These reference compounds were measured under the same HPLC conditions (linear regression analysis for all leachables: R2=0.99). In addition, amounts of co-initiators or co-monomers released from 1 g polymer samples were measured by calculation of the released mass values divided by mass values of the polymer samples. The results were obtained in μg/mL and were also reported in μg/g, relative to the weighted adhesives for data normalization.

The retention time for EDMAB, DMAEMA, and TUMA is 13.3 min, 11.3 min, and 13.5 min FIG. 7A shows the results of cumulative amine co-initiators release from polymers as a function of incubation time in ethanol at 25 C. The cumulative release of EDMAB (EDMAB-0.5: 53.6±4.2 μg/mL) after 60 days is significantly higher (p<0.05) than that of DMAEMA (DMAEMA-0.5: 11.2±3.0 μg/mL). Moreover, no TUMA was detected by HPLC when TUMA was used as co-initiator at 0.5 wt. % or 1.75 wt. %. In addition, there would be 2.68±0.21 mg EDMAB released from 1 gram polymer samples by calculation of the released mass values divided by mass values of polymer samples (FIG. 7B), and 0.56±0.15 mg of DMAEMA would be released from 1 g polymer samples (FIG. 7B).

Ethanol was used in this leachables study to promote the solubility of the hydrophobic compounds (i.e., EDMAB, TUMA, and BisGMA). Based on the HPLC results, more than half of the EDMAB could be released from the polymer, although the chemical stability of EDMAB is comparable with TUMA. Because DMAEMA could be polymerized into the polymer network, there is less release for DMAEMA (11.2%) than EDMAB (53.6%). Furthermore, there was no TUMA release or it was below the detectable limit. TUMA with three methacrylate-urethane groups can be co-polymerized into the polymer network.

Example 6

FIG. 8A is a graph illustrating cumulative HEMA release from dentin adhesives with different co-initiators as a function of incubation time in ethanol, and FIG. 8B is a graph illustrating the data from FIG. 8A transformed by a calculation that divided the mass value of released compounds by the mass values of polymer samples. The same methodology described in Example 5 for determining leaching of compounds from polymers was used here with respect to leaching of HEMA.

The retention time for HEMA is 6.4 min. The cumulative HEMA release at 60 days with 0.5 wt. % of TUMA (TUMA-0.5: 460.9±17.6 μg/mL) is significantly higher (p<0.05) than 1.75 wt. % TUMA, 0.5 wt. % EDMAB, and 0.5 wt. % DMAEMA. When TUMA was increased to 1.75 wt. % (TUMA-1.75: 314.0±11.0 µg/mL), the release of HEMA was similar with that of EDMAB (EDMAB-0.5: 295.0±13.0 µg/mL) and slightly lower than that of DMAEMA (DMAEMA-0.5: 347.3±19.3 µg/mL). Based on the results in FIG. 8A, there would be 23.04±0.88 mg, 17.36±0.96 mg, and 14.75±0.65 mg of HEMA released from 1 g polymer samples after 60 days (FIG. 8B) with TUMA, DMAEMA, and EDMAB as co-initiators (0.5 wt. %), respectively. When TUMA is increased to 1.75 wt. %, HEMA release from 1 g polymer samples after 60 days is 15.70±0.55 mg.

Example 7

FIG. 9 shows the cumulative BisGMA release as a function of time. FIG. 9A is a graph illustrating cumulative BisGMA release from dentin adhesives with different co-initiators as a function of incubation time in ethanol, and FIG. 9B is a graph illustrating the data from FIG. 9A transformed by a calculation that divided the mass value of released compounds by the mass values of polymer samples. The same methodology described in Example 5 for determining leaching of compounds from polymers was used here with respect to leaching of BisGMA.

The retention time for BisGMA is 18.0 min. The cumulative BisGMA release at 60 days with 0.5 wt. % of TUMA (TUMA-0.5: 176.7±9.2 µg/mL) is significantly greater ($p<0.05$) than EDMAB, DMAEMA, and 1.75 wt. % TUMA. EDMAB at 0.5 wt. % (90.5±9.1 µg/mL) showed similar results with TUMA at 1.75 wt. % (91.4±6.8 µg/mL). DMAEMA at 0.5 wt. % showed significantly lower ($p<0.05$) BisGMA release (63.2±4.2 µg/mL). There would be 8.84±0.46 mg, 4.57±0.34 mg, 4.52±0.53 mg, and 3.16±0.21 mg of BisGMA released from 1 g polymer samples after 60 days (FIG. 9B) with 0.5 wt. % TUMA, 1.75 wt. % TUMA, 0.5 wt. % EDMAB, and 0.5 wt. % DMAEMA as co-initiators, respectively.

The monomer release studies of Examples 6 and 7 (and corresponding FIGS. 7A, 7B, 8A, and 8B) indicate more HEMA and BisGMA was released from polymers demonstrating a low degree of conversion (DC). Monomer release is very dependent on DC. With 0.5 wt. % TUMA as the co-initiator, more monomer was released and this was related with the lower DC. By increasing TUMA to 1.75 wt. %, the monomer release was comparable with the samples formulated with EDMAB and DMAEMA.

The release of CQ and DPIHP could not be detected. This might be attributed to the instability of CQ and the ionization of DPIHP in the mobile phase. In regard to the release rate of different compounds, HEMA release (~15 days) is more rapid than BisGMA (~50 days), and DMAEMA release (~20 days) is more rapid than EDMAB (~40 days). The results indicate that more hydrophobic (or larger sized) compounds are released slowly from polymers aged in ethanol. Further, these results indicate that amine co-initiator release could be prevented when TUMA is used as the co-initiator.

Example 8

Real-time in situ monitoring of the visible-light-induced photopolymerization of the adhesive formulations was performed using an infrared spectrometer (Spectrum 400 Fourier transform infrared spectrophotometer, Perkin-Elmer, Waltham, Mass.) at a resolution of 4 cm$^{-1}$. One drop of adhesive solution was placed on the diamond crystal top-plate of an attenuated total reflectance (ATR) accessory (Pike, GladiATR, Pike Technology, Madison, Wis.) and covered with a mylar film. A 40-s exposure to the commercial light-polymerization unit (Spectrum 800®, Dentsply, Milford, Del., ~480-490 nm) at an intensity of 550 mW cm$^{-2}$ was initiated after 50 spectra had been recorded. Real-time IR spectra were recorded continuously for 600 s after light curing began. A time-resolved spectrum collector (Spectrum TimeBase, Perkin-Elmer) was used for continuous and automatic collection of spectra during polymerization. Three replicates were obtained for each adhesive formulation.

The change of the band ratio profile (1637 cm$^{-1}$ (C═C)/ 1715 cm$^{-1}$ (C═O)) was monitored for calibrating the DC of the methacrylate groups. DC was calculated using the following equation, which is based on the decrease in the absorption intensity band ratios before and after light curing. The average of the last 50 values of time-based data points is reported as the DC value at 10 minutes.

$$DC = \left(1 - \frac{Absorbance^{sample}_{1637\,cm^{-1}}/Absorbance^{sample}_{1715\,cm^{-1}}}{Absorbance^{monomer}_{1637\,cm^{-1}}/Absorbance^{monomer}_{1715\,cm^{-1}}}\right) \times 100\%$$

Figure 10:
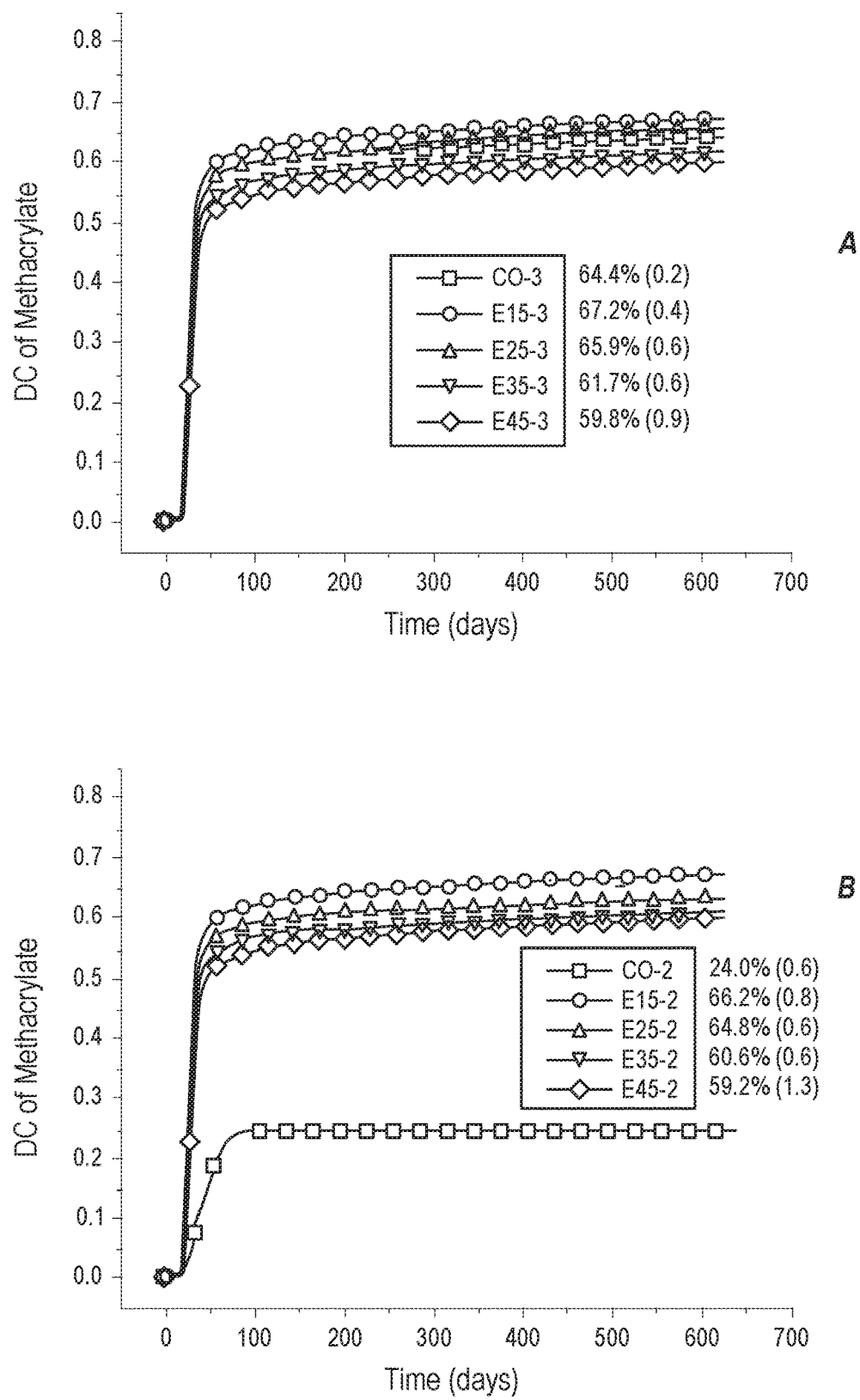
FIG. 10A is a graph illustrating real-time conversion of adhesive resins having a three-component (CQ, DPIHP, and EDMAB) photoinitiator system and TUMA as the co-monomer in accordance with one or more examples disclosed herein.
FIG. 10B is a graph illustrating real-time conversion of adhesive resins having a two-component (CQ and DPIHP) photoinitiator system and TUMA as the co-monomer in accordance with one or more examples disclosed herein.

Polymerization kinetics in regard to degree of conversion (DC) and polymerization rate (Rp) is the first concern with the elimination of the commercial tertiary amine, EDMAB. Here in Example 8, DC was tested. FIG. 10A is a graph illustrating real-time conversion of adhesive resins having a three-component (CQ, DPIHP, and EDMAB) photoinitiator system, and FIG. 10B is a graph illustrating real-time conversion of adhesive resins having a two-component (CQ and DPIHP) photoinitiator system.

The DC of control (CO-3) is 64.4%. When TUMA was used as the co-monomer, at concentrations of 15 (E15-3), 25 (E25-3), 35 (E35-3) and 45 (E45-3) wt %, the DC, after 600 s, was 67.2%, 65.9%, 61.7% and 59.8%, respectively. The DC with two-component photoinitiator system is shown in FIG. 10B. The DC for control with two-component photoinitiator (CO-2) was 24.0%. In comparison, with TUMA as the co-monomer, DC was 66.2%, 64.8%, 60.6% and 59.2% when there were 15 (E15-2), 25 (E25-2), 35 (E35-2) and 45 (E45-2) wt % of TUMA, even with this two-component photoinitiator system.

For control formulations, with and without co-initiator (EDMAB), there is a significant difference in DC. The DC was much lower with the two-component as compared to the three-component-photoinitiator system. When TUMA was used as the co-monomer, DC for experimental adhesives without EDMAB were similar to the formulations with EDMAB. The results indicate that when TUMA was used as a co-monomer, it was not necessary to add the co-initiator, EDMAB. The results support the ability of TUMA to serve simultaneously as a co-monomer and co-initiator.

Example 9

Figure 11:
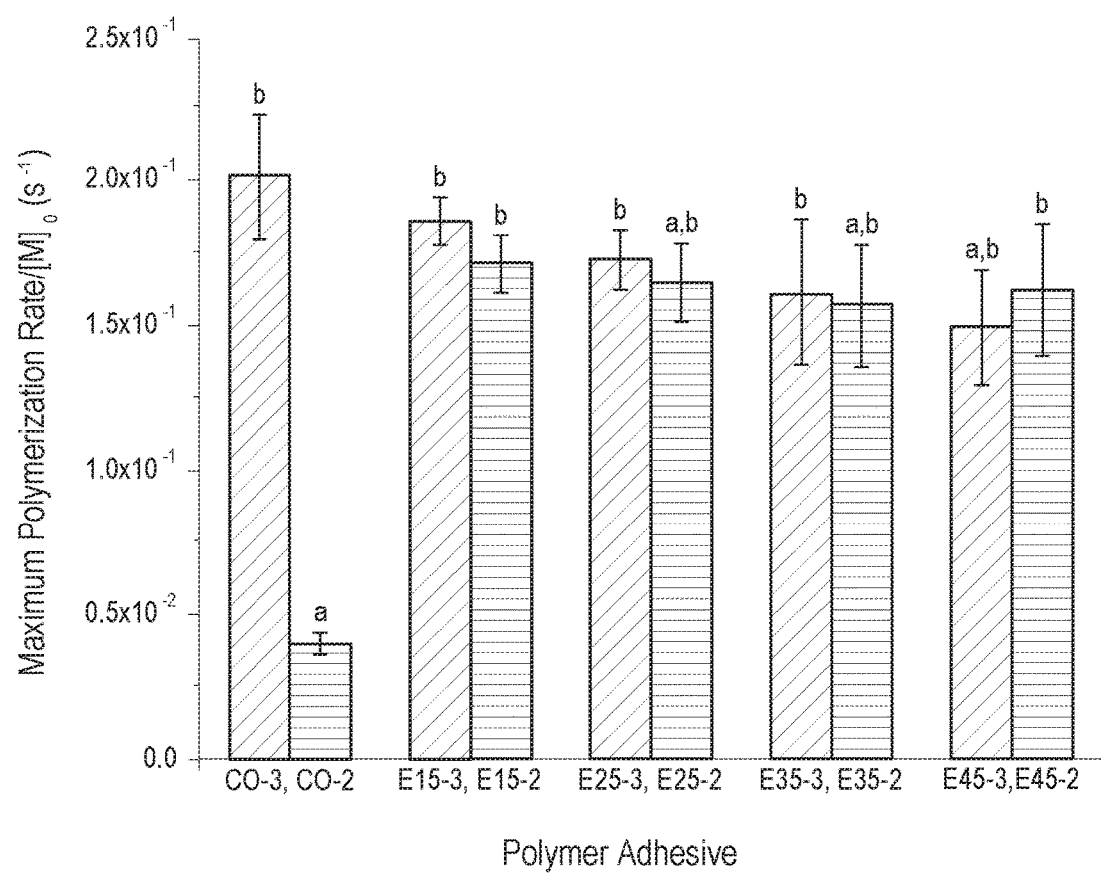
FIG. 11 is a graph illustrating the maximum polymerization rate of adhesive resins with three-component (CQ, DPIHP, and EDMAB) and two-component (CQ and DPIHP) photoinitiator systems when TUMA was used as the co-monomer, where the symbols of Ex-3 and Ex-2 indicate three-component and two-component photoinitiator systems, respectively, in accordance with one or more examples disclosed herein.

Polymerization kinetics in regard to degree of conversion (DC) and polymerization rate (Rp) is the first concern with the elimination of the commercial tertiary amine, EDMAB. Here in Example 9, Rp was tested. FIG. 11 is a graph illustrating the maximum polymerization rate of adhesive resins with three-component (CQ, DPIHP, and EDMAB) and two-component (CQ and DPIHP) photoinitiator systems, where the symbols of Ex-3 and Ex-2 indicate three-component and two-component photoinitiator systems, respectively.

The kinetic data of Example 8 were converted to $Rp/[M]_0$ by taking the first derivative of the time versus the conversion curve, where Rp and $[M]_0$ are the rate of polymerization and the initial monomer concentration, respectively.

For control formulations, Rp with the three-component-photoinitiator system (CO-3) is $2.01 \times 10^{-1}$ s$^{-1}$. However, when there is only a two-component-photoinitiator present, the Rp of the control (CO-2) is $0.40 \times 10^{-1}$ s$^{-1}$. When TUMA was used as the co-monomer, there is no significant difference (p<0.05) in Rp between the three-component (CQ, DPIHP, and EDMAB) and the two-component (CQ and DPIHP) photoinitiator systems with the same content of TUMA. The Rp values for three-component and two-component-photoinitiator systems are 1.86 (E15-3) and $1.71 \times 10^{-1}$ (E15-2), 1.72 (E25-3) and $1.64 \times 10^{-1}$ s$^{-1}$ (E25-2), 1.61 (E35-3) and $1.56 \times 10^{-1}$ s$^{-1}$ (E35-2), 1.49 (E45-3) and $1.62 \times 10^{-1}$ s$^{-1}$ (E45-2), in the presence of 15, 25, 35 and 45 wt % of TUMA, respectively.

For control formulations, with and without co-initiator (EDMAB), there is a significant difference in Rp. The Rp was much lower with the two-component as compared to the three-component-photoinitiator system. When TUMA was used as the co-monomer, Rp for experimental adhesives without EDMAB were similar to the formulations with EDMAB. The results indicate that when TUMA was used as a co-monomer, it was not necessary to add the co-initiator, EDMAB. The results support the ability of TUMA to serve simultaneously as a co-monomer and co-initiator.

mechanical damping, or tan δ (i.e., tan δ=E"/E'). Five specimens of each adhesive formulation were measured, and the results from the five specimens per each formulation were averaged.

FIGS. 12A-D are graphs that illustrate DMA under dry conditions and compare the storage modulus versus temperature curves for adhesives with three-component (CQ, DPIHP, and EDMAB) and two-component (CQ and DPIHP) photoinitiator systems where the wt. % of TUMA co-monomer replacing BisGMA increases sequentially from FIG. 12A through FIG. 12D (i.e., 15 wt % in A, 25 wt. % in B, 35 wt. % in C, and 45 wt. % in D).

Figure 12:
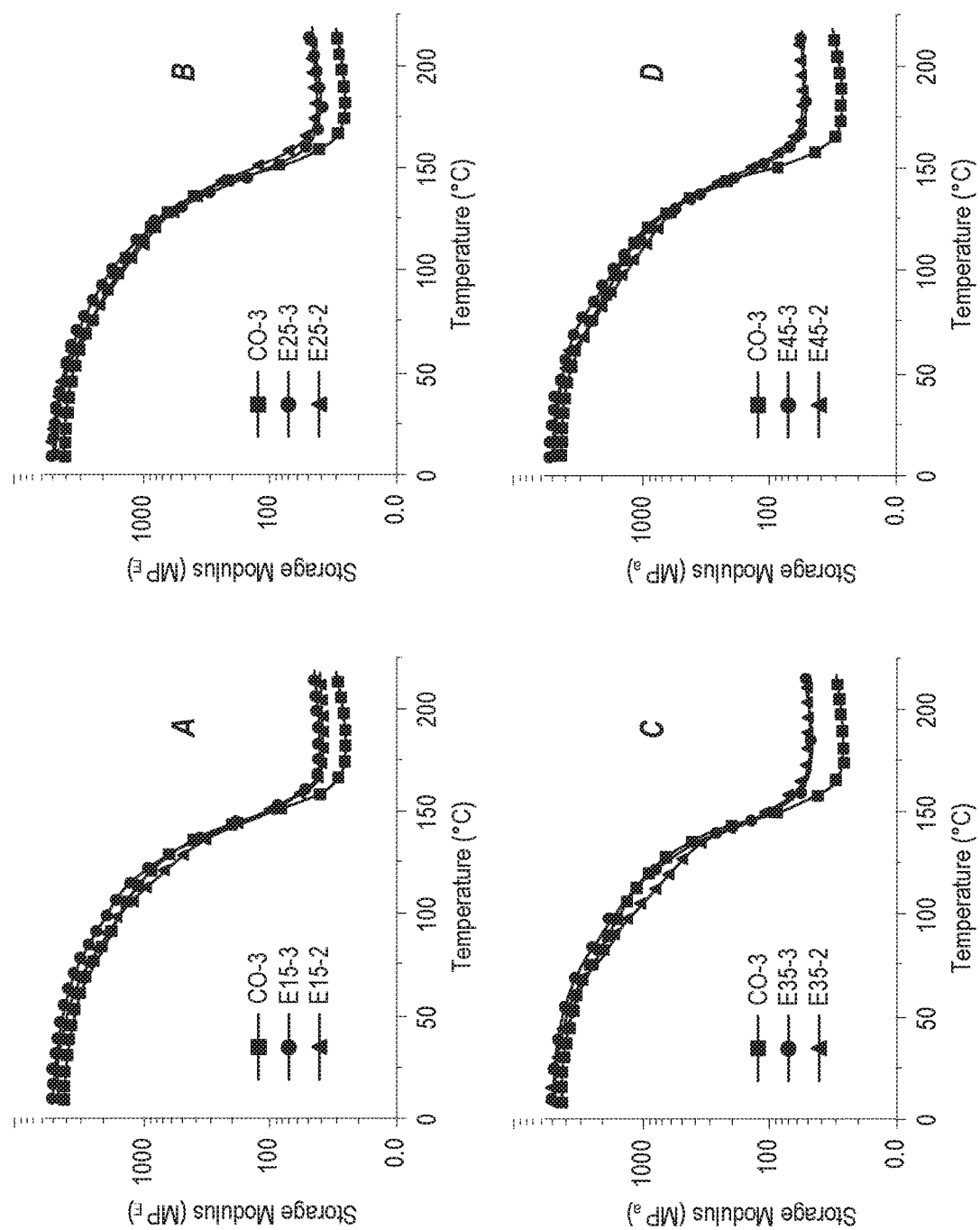
FIGS. 12A-D are graphs that illustrate dynamic mechanical analysis under dry conditions and compare the storage modulus versus temperature curves for adhesives with three-component (CQ, DPIHP, and EDMAB) and two-component (CQ and DPIHP) photoinitiator systems where the wt. % of TUMA co-monomer replacing BisGMA increases sequentially from FIG. 12A through FIG. 12D (i.e., 15 wt % in A, 25 wt. % in B, 35 wt. % in C, and 45 wt. % in D) in accordance with one or more examples disclosed herein.

The results of DMA under dry conditions for all adhesives are shown in FIG. 12 and Table 1. From FIG. 12, it is apparent that the storage moduli of experimental adhesives at rubbery region (>180° C., ~40-50 MPa) for both three- and two-component-photoinitiator systems are higher than control (27.1 MPa). The storage moduli at the rubbery region increased with increasing TUMA content. Moreover, with the same content of TUMA, there is no statistically significant difference in the storage moduli at rubbery region between three- and two-component-photoinitiator systems.

As shown in Table 1, Tg of control (CO-3) is 151.5° C. When TUMA was used as the co-monomer, Tg was comparable with control for both three- (~149-150° C.) and two- (~150-153° C.) component initiator systems. There was no statistically significant difference for tan δ (Table 1) for all formulations.

TABLE 1

DMA results under dry conditions

| Sample | Storage modulus at 25° C. (MPa) × 10$^3$ | Storage modulus at 37° C. (MPa) × 10$^3$ | Storage modulus at 180° C. (MPa) | Tg (° C.)[a] | Height of tan δ peak |
|---|---|---|---|---|---|
| CO-3[d] | 4.16 ± 0.22 | 3.96 ± 0.21 | 27.1 ± 1.0 | 151.5 ± 1.1 | 0.63 ± 0.02 |
| E15-3[e] | 4.65 ± 0.04[b] | 4.39 ± 0.05[b] | 40.5 ± 2.3[b] | 150.3 ± 0.2 | 0.63 ± 0.02 |
| E25-3 | 4.59 ± 0.09[b] | 4.31 ± 0.09[b] | 43.9 ± 1.8[b] | 148.8 ± 0.4[b] | 0.64 ± 0.03 |
| E35-3 | 4.58 ± 0.11[b] | 4.29 ± 0.10[b] | 47.9 ± 3.5[b] | 148.2 ± 0.7[b] | 0.63 ± 0.03 |
| E45-3 | 4.57 ± 0.07[b] | 4.28 ± 0.70[b] | 50.7 ± 1.4[b] | 149.4 ± 0.5[b] | 0.64 ± 0.02 |
| E15-2[f] | 4.54 ± 0.11[b] | 4.26 ± 0.09 | 38.4 ± 1.5[b] | 152.0 ± 1.1 | 0.61 ± 0.02 |
| E25-2 | 4.54 ± 0.03[b] | 4.26 ± 0.03[b] | 42.3 ± 1.5[b] | 152.5 ± 0.9[c] | 0.65 ± 0.02 |
| E35-2 | 4.50 ± 0.11[b] | 4.21 ± 0.10 | 47.4 ± 2.0[b] | 150.4 ± 0.5[c] | 0.64 ± 0.02 |
| E45-2 | 4.43 ± 0.19 | 4.15 ± 0.21 | 48.9 ± 1.7[b] | 151.4 ± 0.8[c] | 0.63 ± 0.02 |

Values are mean (±standard deviation) for n = 5 in each group.
[a]The glass transition temperatures (Tg) values of the polymer networks were taken to be the maximum of the tan δ versus temperature curve, which was determined by using a dynamic mechanical analyzer.
[b]Significant (p < 0.05) difference from CO-3.
[c]Significant (p < 0.05) difference from Ex-3 with the same content of TUMA.
[d,e]Formulations of CO-3 and Ex-3 group were prepared with three-component photoinitiator system, containing 0.5 wt % of EDMAB.
[f]Formulations of Ex-2 group were prepared with two-component photoinitiator system, containing only 0.5 wt % of CQ and 1.0 wt % of DPIHP (No EDMAB).

Example 10

The viscoelastic properties of the adhesives were characterized using dynamic mechanical analysis (DMA) Q800 (TA Instruments, New Castle, USA) with a 3-point bending clamp. The cylinder beam specimens (1 mm×15 mm) were divided into two groups. The first group consisted of dry samples. These specimens were tested using a standard 3-point bending clamp. The test temperature was varied from 10° to 220° C. with a ramping rate of 3° C./min, a frequency of 1 Hz, an amplitude of 15 μm, and a pre-load of 0.01 N.

The properties measured under this oscillating loading were storage modulus (E') and tan δ. The ratio of the loss modulus (E") to the storage modulus E' is referred to as the When TUMA was used as the co-monomer, the storage moduli at the rubbery region were higher than the control when the specimens were tested under dry conditions. The results suggest that the crosslinking density was increased by introducing this new co-monomer that contains three methacrylate-urethane groups. With the same content of TUMA, the storage moduli at the rubbery region were similar between three-component and two-component photoinitiator systems. These results suggest that the crosslinking density is not influenced by co-initiator (EDMAB) in the presence of TUMA. Under these conditions, EDMAB could be eliminated from the formulation without compromising the dynamic mechanical properties of the dentin adhesive.

Example 11

The viscoelastic properties of the adhesives were characterized using DMA Q800 (TA Instruments, New Castle, USA) with a 3-point bending clamp. The cylinder beam specimens (1 mm×15 mm) were divided into two groups. The second group consisted of wet samples, which were immersed in deionized water and stored at 37° C. for five days. The water was changed daily. The wet samples were tested by 3-point bending, using a water submersion clamp. The test temperature was varied from 10° to 80° C. with a ramping rate of 1.5° C./min at a frequency of 1 Hz. The properties measured under this oscillating loading were storage modulus (E') and tan δ. The ratio of the loss modulus (F') to the storage modulus E' is referred to as the mechanical damping, or tan δ (i.e., tan δ=E"/E'). Five specimens of each adhesive formulation were measured, and the results from the five specimens per each formulation were averaged.

FIGS. 13A-D are graphs that illustrate DMA under wet conditions and compare the storage modulus versus temperature curves for adhesives with three-component (CQ, DPIHP, and EDMAB) and two-component (CQ and DPIHP) photoinitiator systems where the wt. % of TUMA co-monomer replacing BisGMA increases sequentially from FIG. 13A through FIG. 13D (i.e., 15 wt % in A, 25 wt. % in B, 35 wt. % in C, and 45 wt. % in D) in accordance with one or more examples disclosed herein.

Figure 13:
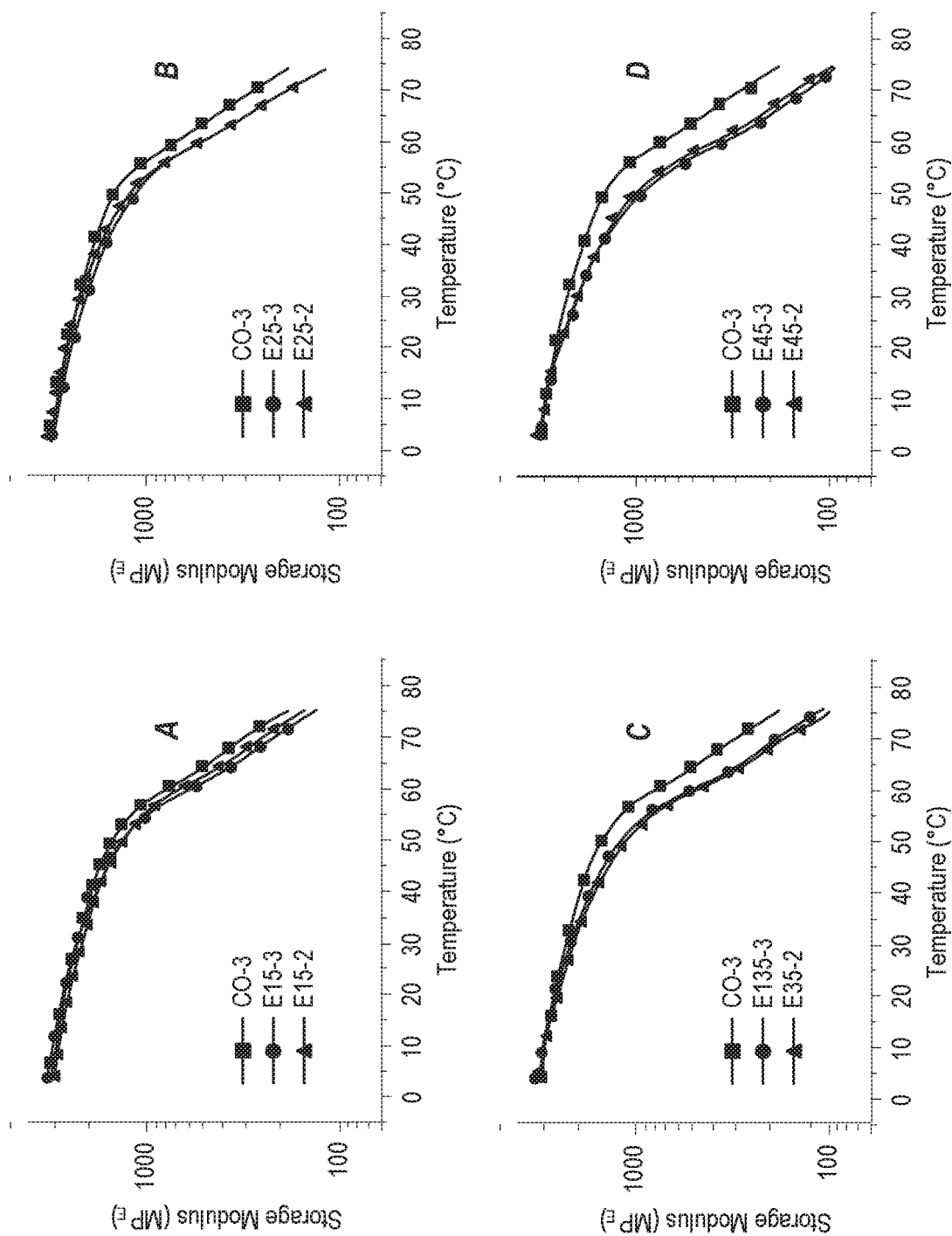
FIGS. 13A-D are graphs that illustrate dynamic mechanical analysis under wet conditions and compare the storage modulus versus temperature curves for adhesives with three-component (CQ, DPIHP, and EDMAB) and two-component (CQ and DPIHP) photoinitiator systems where the wt. % of TUMA co-monomer replacing BisGMA increases sequentially from FIG. 13A through FIG. 13D (i.e., 15 wt % in A, 25 wt. % in B, 35 wt. % in C, and 45 wt. % in D) in accordance with one or more examples disclosed herein.

The results of DMA under wet condition are shown in FIG. 13 and summarized in Table 2. The storage modulus values for the experimental formulations are lower than the control (CO-3) at 37° C. and 70° C. Moreover, with the same content of TUMA, there is no statistically significant difference in storage moduli at rubbery region (70° C. under wet conditions) between three-component and two-component photoinitiator systems. As shown in Table 2, under wet conditions Tg decreases with an increase in TUMA content. Meanwhile, the intensity of tan δ peaks increase with increasing TUMA.

12, the decreased mechanical properties noted with the experimental formulations, under wet conditions, could be associated with more water sorption. Water could act as a plasticizer in the crosslinked network. Water is also known to facilitate the degradation of methacrylate adhesives, which have numerous ester groups that are subject to both hydrolytic degradation and enzymatic hydrolysis. In addition, the broad glass transition curves for all the samples tested here indicate that the polymer networks are heterogeneous with glass transition occurring over a broad range of temperature. This could be attributed to the polymerization of multi-functional monomers which can produce very heterogeneous networks, i.e., networks that exhibit regions that are highly crosslinked and regions with limited crosslinking. In other words, highly increased crosslink density, as noted in the dry experimental samples, may be accompanied by a sacrifice in homogeneity of the polymer network structure and a significantly weaker structure in the loosely crosslinked regions potentially causing premature failure, especially with the increased water sorption. Under these conditions, the adhesive/dentin bond could have limited structural integrity and durability.

Example 12

Water sorption was measured using cylindrical beam specimens (1 mm×15 mm). Five specimens were used for each adhesive formulation. The specimens were immersed in deionized water and stored at 37° C. The water was changed daily. After five days of prewash, the polymer specimens were allowed to dry in the vacuum chamber at 37° C. until a constant weight ($m_{1dry}$) was obtained. After prewash, the dry specimens were then immersed in deionized water and stored at room temperature. At fixed time intervals (3, 6, 24, 48, 72 and 168 h), the polymer specimens were retrieved, blotted dry to remove excess liquid, weighed ($m_{2wet}$), and re-immersed in the water. The value (%) for solubility and mass change (water sorption) were calculated as:

TABLE 2

DMA results under wet conditions

| Sample | Storage modulus at 25° C. (MPa) × $10^3$ | Storage modulus at 37° C. (MPa) × $10^3$ | Storage modulus at 70° C. (MPa) × $10^2$ | Tg (° C.)[a] | Intensity of tan δ at 70° C. |
|---|---|---|---|---|---|
| CO-3[d] | 2.38 ± 0.05 | 1.98 ± 0.05 | 3.39 ± 0.35 | 58.9 ± 0.4 | 0.40 ± 0.02 |
| E15-3[e] | 2.35 ± 0.07 | 1.87 ± 0.05[b] | 2.13 ± 0.15[b] | 57.8 ± 0.2[b] | 0.47 ± 0.01[b] |
| E25-3 | 2.27 ± 0.06 | 1.79 ± 0.04[b] | 2.15 ± 0.16[b] | 57.8 ± 0.1[b] | 0.48 ± 0.01[b] |
| E35-3 | 2.22 ± 0.08[b] | 1.74 ± 0.06[b] | 1.86 ± 0.14[b] | 57.5 ± 0.3[b] | 0.50 ± 0.01[b] |
| E45-3 | 2.21 ± 0.03[b] | 1.66 ± 0.03[b] | 1.42 ± 0.12[b] | 55.9 ± 0.1[b] | 0.53 ± 0.01[b] |
| E15-2[f] | 2.29 ± 0.05 | 1.85 ± 0.04[b] | 2.39 ± 0.22[b] | 58.0 ± 0.3[b] | 0.46 ± 0.01[b] |
| E25-2 | 2.33 ± 0.04 | 1.85 ± 0.04[b] | 2.05 ± 0.16[b] | 57.9 ± 0.1[b] | 0.49 ± 0.01[b] |
| E35-2 | 2.19 ± 0.08[b] | 1.70 ± 0.06[b] | 1.68 ± 0.17[b] | 57.2 ± 0.4[b] | 0.51 ± 0.01[b] |
| E45-2 | 2.21 ± 0.04[b] | 1.69 ± 0.01[b] | 1.63 ± 0.11[b] | 56.2 ± 0.3[b] | 0.52 ± 0.01[b] |

Values are mean (±standard deviation) for n = 5 in each group.
[a]The glass transition temperatures (Tg) values of the polymer networks were taken to be the minimum of the Deriv. storage modulus versus temperature curve determined using a dynamic mechanical analyzer.
[b]Significant (p < 0.05) difference from CO-3.
[c]Significant (p < 0.05) difference from Ex-3 with the same content of TUMA.
[d,e]Formulations of CO-3 and Ex-3 group were prepared with three-component photoinitiator system, containing 0.5 wt % of EDMAB.
[f]Formulations of Ex-2 group were prepared with two-component photoinitiator system, containing only 0.5 wt % of CQ and 1.0 wt % of DPIHP (No EDMAB).

Since water or saliva is always present in the oral environment, it may be important to understand the viscoelastic properties of polymers under wet conditions. The setup with three-point bending water-submersion clamp used in this example is expected to simulate the wet environment of the mouth. In this example and with some reference to Example $$\text{Mass change}(\%) = 100\frac{m_{2wet} - m_{1dry}}{m_{1dry}} = \text{Water sorption}(\%)$$

Results of water sorption of resin polymers cured with different weight contents of TUMA are illustrated in FIG. 14. Therein, symbols E15, E25, E35, and E45 represent 15, 25, 35, and 45 wt. % of TUMA, respectively, in the tested compositions; formulations depicted in FIG. 14A had a three-component (CQ, DPIHP, and EDMAB) initiator system, and formulations depicted in FIG. 14B had a two-component (CQ and DPIHP) initiator system. The water sorption value for the control formulation is 10.2%. Water sorption increased with increasing TUMA content to 10.7% (E15-3), 11.4% (E25-3), 12.4% (E35-3) and 12.9% (E45-3) with the three-component initiator system. The water sorption values are 11.3% (E15-2), 12.1% (E25-2), 12.3% (E35-2) and 13.2% (E45-2) with the two-component initiator system. The control formulations consisted of HEMA and BisGMA with a mass ratio of 45/55, which is similar to widely used commercial dentin adhesives. It should be noted that there are two control formulations: C0-3 is HEMA/BisGMA 45/55 and 3-component photoinitiator system; C0-2 is HEMA/BisGMA 45/55 and 2-component photoinitiator system. These controls were used as a comparison to the experimental adhesive resins (Ex-3 or Ex-2), in which x represents the weight percentage of synthesized co-monomer (TUMA) to replace part of BisGMA. For example, E15-3, 15 wt % of BisGMA was replaced by TUMA, HEMA/TUMA/BisGMA=45/15/40 wt %. CQ, EDMAB and DPIHP at concentrations 0.5, 0.5 and 1.0 wt % with respect to the total amount of monomers, were used as a three-component-photoinitiator system (C0-3 and Ex-3 groups). The two-component-photoinitiator system contains only CQ (0.5 wt %) and DPIHP (1.0 wt %) (C0-2 and Ex-2 groups).

5. Definitions

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z or a mixture thereof. Likewise, it is understood that, in any compound described, all tautomeric forms are also intended to be included.

It is to be understood that where compounds disclosed herein have unfilled valences, then the valences are to be filled with hydrogen or isotopes thereof, e.g., hydrogen-1 (protium) and hydrogen-2 (deuterium).

It is understood that the compounds described herein can be labeled isotopically. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and compositions described herein include crystalline forms, amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. In addition, the compounds provided herein can exist in unsolvated as well as solvated forms. In general, the solvated forms are considered equivalent to the unsolvated forms for the purposes of the compounds and methods provided herein.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

As used herein, any "R" group(s) represents substituents that can be attached to the indicated atom. Unless otherwise specified, an R group may be substituted or unsubstituted.

Whenever a group is described as being "substituted" that group may be substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

"Lower alkylene groups" refer to a $C_1$-$C_{25}$ straight-chained alkyl tethering groups, such as —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys is methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —$NH_2$ group or a —NH— group.

As used herein, the term "hydroxy" or "hydroxyl" refers to a —OH group.

As used herein, the term "ether" refers to a —O— group.

A "cyano" group refers to a —CN group.

A "carbonyl" or an "oxo" group refers to a C=O group.

An "amido" group as used herein refers to an organic amide where a carbonyl group is bonded to nitrogen. The nitrogen of the amideo group may not be connected to any R group (e.g., acetamide); may be connected to one R group, resulting in an amino group; or may be connected to two R groups.

The term "azido" as used herein refers to a —$N_3$ group.

As used herein, "aminoalkyl" refers to an amino group connected, as a substituent, via a lower alkylene group. Examples include $H_2N$-alkyl- with the term alkyl defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A co-initiator for use in preparing a polymer, said co-initiator comprising:
    a tertiary amine core; and
    two or more pendant, terminal methacrylate groups.

2. A co-initiator as in claim 1, wherein the co-initiator also acts as a co-monomer in a co-polymerization reaction.

3. A co-initiator as in claim 1, the co-initiator consisting of the molecular structure of Formula 1, or a derivative thereof,
    wherein $R_1$ is selected from the group consisting of: hydrogen, an alkyl, a hydroxyl, and an amino; and
    wherein $R_2$ is selected from the group consisting of: an ether, an amido, an amino, an alkyl-ether, an alkyl-amido, an alkyl-amino, an ether-alkyl, an amido-alkyl, an amino-alkyl, an alkyl-ether-alkyl, an alkyl-amido-alkyl, and an alkyl-amino-alkyl.

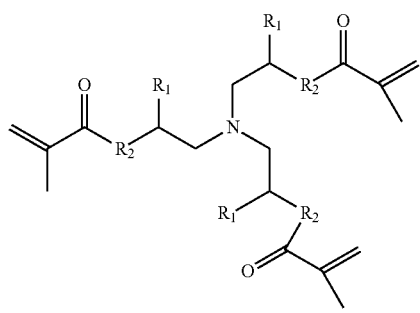

Formula 1

4. A co-initiator as in claim 1, the co-initiator consisting of the molecular structure of Formula 2, or a derivative thereof,
  wherein $R_1$ is selected from the group consisting of: hydrogen, an alkyl, a hydroxyl, and an amino; and
  wherein $R_2$ is selected from the group consisting of: an ether and an amino.

monomers or oligomers having one or more ethylenically unsaturated groups, di-acrylates and methacrylates, tri-acrylates and methacrylates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyl eneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("Bis-GMA"), triethylene glycol dimethacrylate (TEGDMA), 1,6-bis-[2-methacryloyloxyethoxycarbonylamino]-2,4,4-trimethylhexane (UDMA), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acry-

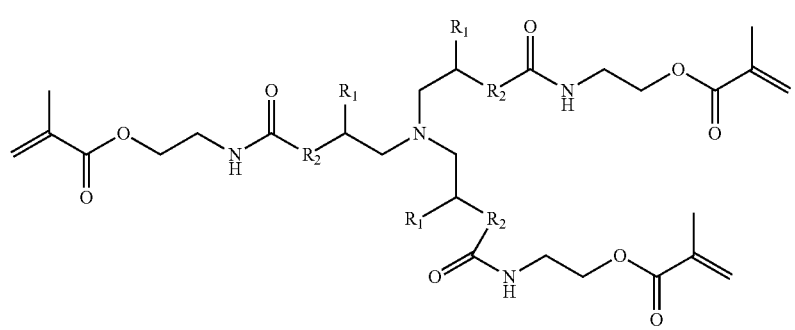

Formula 2

5. A co-initiator as in claim 1, the co-initiator consisting of the molecular structure of Formula 3, or a derivative thereof.

lates and bis-methacrylates of polyethylene glycols of molecular weight 200-500, copolymerizable mixtures of acrylated monomers, copolymerizable acrylated oligomers,

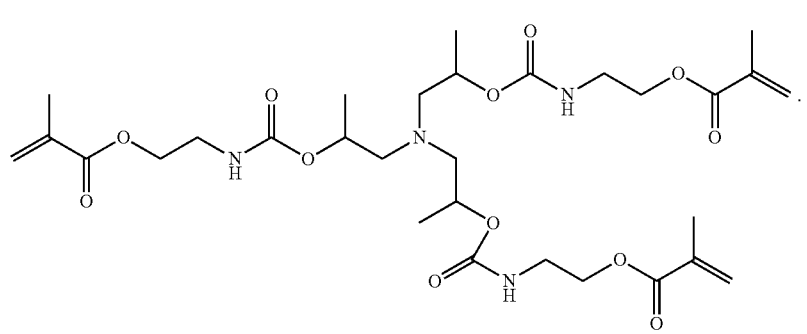

Formula 3

6. A composition for use in preparing a light curable dental resin composite, comprising:
  a co-initiator, the co-initiator comprising:
    a tertiary amine core; and
    two or more pendant, terminal methacrylate groups.
7. The composition as in claim 6, further comprising a photosensitizer and a diaryliodonium or a sulfonium salt.
8. The composition as in claim 6, wherein the composition further includes monomers or oligomers selected from phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.
9. The composition as in claim 8, wherein the monomers or oligomers comprise at least one of 2-hydroxyethyl methacrylate (HEMA) and diglycidyl methacrylate of bis-phenol (BisGMA).

10. The composition as in claim 8, wherein the monomers or oligomers comprise monomers or oligomers of the co-initiator of claim 6.

11. The composition as in claim 10, wherein the monomers or oligomers further comprise at least one of 2-hydroxyethyl methacrylate (HEMA) or diglycidyl methacrylate of bis-phenol (BisGMA).

12. The composition as in claim 11, further comprising a photosensitizer and a diaryliodonium or a sulfonium salt.

13. A method of preparing a light cured polymer-based dental restorative material, comprising:
combining a set of one or more monomers or oligomers with a photoinitiator system, the photoinitiator system comprising:
a co-initiator comprising a tertiary amine core and two or more pendant, terminal methacrylate groups;
exposing the combined set of one or more monomers or oligomers and photoinitiator system to light so as to polymerize the set of one or more monomers or oligomers to yield a polymer.

14. The method as in claim 13, wherein the polymer is prepared in a mouth of a subject.

15. The method as in claim 13, wherein the one or more monomers or oligomers are selected from monomers or oligomers having one or more ethylenically unsaturated groups, di-acrylates and methacrylates, tri-acrylates and methacrylates, poly-acrylates and methacrylates, 2-hydroxyethyl methacrylate (HEMA), methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, diurethane dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol ("BisGMA"), triethylene glycol dimethacrylate (TEGDMA), 1,6-bis-[2-methacryloyloxyethoxycarbonylamino]-2,4,4-trimethylhexane (UDMA), bis[1-(2-acryloxy)]-p-ethoxyphenyldimethylmethane, bis[1-(3-acryloxy-2-hydroxy)]-p-propoxyphenyldimethylmethane, trishydroxyethyl-isocyanurate trimethacrylate, the bis-acrylates and bis-methacrylates of polyethylene glycols of molecular weight 200-500, copolymerizable mixtures of acrylated monomers, copolymerizable acrylated oligomers, phosphoric acid derivatives and carboxylic acid derivatives of ethylenically unsaturated monomers, vinyl compounds, styrene, diallyl phthalate, divinyl succinate, divinyl adipate and divinylphthalate, and combinations thereof.

16. The method as in claim 15, wherein the one or more monomers or oligomers are 2-hydroxyethyl methacrylate (HEMA), diglycidyl methacrylate of bis-phenol (BisGMA), or combinations thereof.

17. The method as in claim 13, wherein the photoinitiator system further comprises a photosensitizer.

18. The method as in claim 17, wherein the photoinitiator system further comprises a diaryliodonium or a sulfonium salt.

19. The method as in claim 13, wherein the set of monomers or oligomers comprises the co-initiator.

20. The method as in claim 13, wherein the polymer leaches substantially no co-initiator following polymerization.

* * * * *